(12) United States Patent
Umbarger et al.

(10) Patent No.: US 10,227,635 B2
(45) Date of Patent: Mar. 12, 2019

(54) CAPTURE REACTIONS

(75) Inventors: Mark Umbarger, Brookline, MA (US); Gregory Porreca, Cambridge, MA (US); Charles Towne, Shrewsbury, MA (US); George Church, Brookline, MA (US)

(73) Assignee: Molecular Loop Biosolutions, LLC, Cambridge, MA (US)

( * ) Notice: Subject to any disclaimer, the term of this patent is extended or adjusted under 35 U.S.C. 154(b) by 0 days.

(21) Appl. No.: 13/448,961

(22) Filed: Apr. 17, 2012

(65) Prior Publication Data

US 2013/0274146 A1  Oct. 17, 2013

Related U.S. Application Data

(60) Provisional application No. 61/624,778, filed on Apr. 16, 2012.

(51) Int. Cl.
| | | |
|---|---|---|
| *C12Q 1/6816* | (2018.01) | |
| *C12Q 1/6813* | (2018.01) | |
| *C12Q 1/6806* | (2018.01) | |
| *C12Q 1/6869* | (2018.01) | |

(52) U.S. Cl.
CPC ......... *C12Q 1/6816* (2013.01); *C12Q 1/6806* (2013.01); *C12Q 1/6813* (2013.01); *C12Q 1/6869* (2013.01)

(58) Field of Classification Search
CPC ... C12Q 1/6806; C12Q 1/6813; C12Q 1/6816
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,988,617 | A | 1/1991 | Landegren et al. |
| 5,234,809 | A | 8/1993 | Boom et al. |
| 5,242,794 | A | 9/1993 | Whiteley et al. |
| 5,494,810 | A | 2/1996 | Barany et al. |
| 5,583,024 | A | 12/1996 | McElroy et al. |
| 5,604,097 | A | 2/1997 | Brenner |
| 5,636,400 | A | 6/1997 | Young |
| 5,674,713 | A | 10/1997 | McElroy et al. |
| 5,695,934 | A | 12/1997 | Brenner |
| 5,700,673 | A | 12/1997 | McElroy et al. |

(Continued)

FOREIGN PATENT DOCUMENTS

| | | |
|---|---|---|
| EP | 1321477 A1 | 6/2003 |
| EP | 1564306 A2 | 8/2005 |

(Continued)

OTHER PUBLICATIONS

Sargent et al. (Methods in Enzymology, 1987, 152:423-432).*

(Continued)

*Primary Examiner* — Jeremy C Flinders
(74) *Attorney, Agent, or Firm* — Brown Rudnick LLP; Thomas C. Meyers

(57) ABSTRACT

The invention generally relates to methods of performing a capture reaction. In certain embodiments, the method involves obtaining a nucleic acid, fragmenting the nucleic acid, and capturing a target sequence on the nucleic acid fragment using a capture moiety, such as a molecular inversion probe.

6 Claims, 3 Drawing Sheets

Specification includes a Sequence Listing.

(56) References Cited

U.S. PATENT DOCUMENTS

| | | |
|---|---|---|
| 5,701,256 A | 12/1997 | Marr et al. |
| 5,830,064 A | 11/1998 | Bradish et al. |
| 5,846,719 A | 12/1998 | Brenner et al. |
| 5,863,722 A | 1/1999 | Brenner |
| 5,866,337 A | 2/1999 | Schon |
| 5,869,252 A | 2/1999 | Bouma et al. |
| 5,871,921 A | 2/1999 | Landegren |
| 5,993,611 A | 11/1999 | Moroney, III et al. |
| 6,100,099 A | 8/2000 | Gordon et al. |
| 6,138,077 A | 10/2000 | Brenner |
| 6,150,516 A | 11/2000 | Brenner et al. |
| 6,172,214 B1 | 1/2001 | Brenner |
| 6,172,218 B1 | 1/2001 | Brenner |
| 6,197,508 B1 | 3/2001 | Stanley |
| 6,210,891 B1 | 4/2001 | Nyren et al. |
| 6,223,128 B1 | 4/2001 | Allex et al. |
| 6,235,472 B1 | 5/2001 | Landegren et al. |
| 6,235,475 B1 | 5/2001 | Brenner et al. |
| 6,235,501 B1 | 5/2001 | Gautsch et al. |
| 6,258,568 B1 | 7/2001 | Nyren |
| 6,274,320 B1 | 8/2001 | Rothberg et al. |
| 6,306,597 B1 | 10/2001 | Macevicz |
| 6,352,828 B1 | 3/2002 | Brenner |
| 6,361,940 B1 | 3/2002 | Van Ness et al. |
| 6,403,320 B1 | 6/2002 | Read et al. |
| 6,489,105 B1 | 12/2002 | Matlashewski et al. |
| 6,558,928 B1 | 5/2003 | Landegren |
| 6,582,938 B1 | 6/2003 | Su et al. |
| 6,714,874 B1 | 3/2004 | Myers et al. |
| 6,719,449 B1 | 4/2004 | Laugharn, Jr. et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,858,412 B2 | 2/2005 | Willis et al. |
| 6,911,345 B2 | 6/2005 | Quake et al. |
| 6,913,879 B1 | 7/2005 | Schena |
| 6,948,843 B2 | 9/2005 | Laugharn, Jr. et al. |
| 7,034,143 B1 | 4/2006 | Preparata et al. |
| 7,041,481 B2 | 5/2006 | Anderson et al. |
| 7,049,077 B2 | 5/2006 | Yang |
| 7,057,026 B2 | 6/2006 | Barnes et al. |
| 7,071,324 B2 | 7/2006 | Preparata et al. |
| 7,074,564 B2 | 7/2006 | Landegren |
| 7,115,400 B1 | 10/2006 | Adessi et al. |
| 7,169,560 B2 | 1/2007 | Lapidus et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| RE39,793 E | 8/2007 | Brenner |
| 7,264,929 B2 | 9/2007 | Rothberg et al. |
| 7,282,337 B1 | 10/2007 | Harris |
| 7,297,518 B2 | 11/2007 | Quake et al. |
| 7,320,860 B2 | 1/2008 | Landegren |
| 7,323,305 B2 | 1/2008 | Leamon et al. |
| 7,335,762 B2 | 2/2008 | Rothberg et al. |
| 7,351,528 B2 | 4/2008 | Landegren |
| 7,393,665 B2 | 7/2008 | Brenner |
| 7,510,829 B2 | 3/2009 | Faham et al. |
| 7,537,897 B2 | 5/2009 | Brenner et al. |
| 7,544,473 B2 | 6/2009 | Brenner |
| 7,582,431 B2 | 9/2009 | Drmanac et al. |
| 7,598,035 B2 | 10/2009 | Macevicz |
| 7,666,593 B2 | 2/2010 | Lapidus |
| 7,700,323 B2 | 4/2010 | Willis et al. |
| 7,776,616 B2 | 8/2010 | Heath et al. |
| RE41,780 E | 9/2010 | Anderson et al. |
| 7,790,388 B2 | 9/2010 | Landegren et al. |
| 7,809,509 B2 | 10/2010 | Milosavljevic |
| 7,835,871 B2 | 11/2010 | Kain et al. |
| 7,862,999 B2 | 1/2011 | Zheng |
| 7,865,534 B2 | 1/2011 | Chandra et al. |
| 7,883,849 B1 | 2/2011 | Dahl |
| 7,957,913 B2 | 6/2011 | Chinitz et al. |
| 7,960,120 B2 | 6/2011 | Rigatti et al. |
| 7,993,880 B2 | 8/2011 | Willis et al. |
| 8,024,128 B2 | 9/2011 | Rabinowitz et al. |
| 8,165,821 B2 | 4/2012 | Zhang |
| 8,209,130 B1 | 6/2012 | Kennedy et al. |
| 2001/0007742 A1 | 7/2001 | Landergren |
| 2001/0046673 A1 | 11/2001 | French et al. |
| 2002/0001800 A1 | 1/2002 | Lapidus |
| 2002/0164629 A1 | 11/2002 | Quake et al. |
| 2002/0182609 A1 | 12/2002 | Arcot |
| 2002/0187496 A1 | 12/2002 | Andersson et al. |
| 2002/0190663 A1 | 12/2002 | Rasmussen |
| 2003/0166057 A1 | 9/2003 | Hildebrand et al. |
| 2003/0177105 A1 | 9/2003 | Xiao et al. |
| 2003/0203370 A1 | 10/2003 | Yakhini et al. |
| 2003/0224384 A1 | 12/2003 | Sayood et al. |
| 2004/0106112 A1 | 6/2004 | Nilsson |
| 2004/0121373 A1* | 6/2004 | Friedlander ............ C12N 15/10 435/6.12 |
| 2004/0142325 A1 | 7/2004 | Mintz et al. |
| 2004/0152108 A1 | 8/2004 | Keith et al. |
| 2004/0209299 A1 | 10/2004 | Pinter et al. |
| 2005/0026204 A1 | 2/2005 | Landegren |
| 2005/0032095 A1 | 2/2005 | Wigler et al. |
| 2005/0048505 A1 | 3/2005 | Fredrick et al. |
| 2005/0059048 A1 | 3/2005 | Gunderson et al. |
| 2005/0100900 A1 | 5/2005 | Kawashima et al. |
| 2005/0112590 A1 | 5/2005 | Boon |
| 2005/0244879 A1 | 11/2005 | Schumm et al. |
| 2006/0019304 A1 | 1/2006 | Hardenbol |
| 2006/0024681 A1 | 2/2006 | Smith et al. |
| 2006/0078894 A1 | 4/2006 | Winkler et al. |
| 2006/0177837 A1 | 8/2006 | Borozan et al. |
| 2006/0183132 A1 | 8/2006 | Fu |
| 2006/0192047 A1 | 8/2006 | Goossen |
| 2006/0292585 A1 | 12/2006 | Nautiyal |
| 2006/0292611 A1 | 12/2006 | Berka et al. |
| 2007/0020640 A1 | 1/2007 | McCloskey et al. |
| 2007/0042369 A1 | 2/2007 | Reese et al. |
| 2007/0092883 A1 | 4/2007 | Schouten et al. |
| 2007/0114362 A1 | 5/2007 | Feng et al. |
| 2007/0128624 A1 | 6/2007 | Gormley et al. |
| 2007/0161013 A1 | 7/2007 | Hantash |
| 2007/0166705 A1 | 7/2007 | Milton et al. |
| 2007/0225487 A1 | 9/2007 | Nilsson |
| 2007/0264653 A1 | 11/2007 | Berlin et al. |
| 2008/0003142 A1 | 1/2008 | Link et al. |
| 2008/0014589 A1 | 1/2008 | Link et al. |
| 2008/0076118 A1 | 3/2008 | Tooke et al. |
| 2008/0081330 A1 | 4/2008 | Kahvejian |
| 2008/0269068 A1 | 10/2008 | Church et al. |
| 2008/0280955 A1 | 11/2008 | McCamish |
| 2008/0293589 A1 | 11/2008 | Shapero |
| 2009/0019156 A1 | 1/2009 | Mo et al. |
| 2009/0026082 A1 | 1/2009 | Rothberg et al. |
| 2009/0098551 A1 | 4/2009 | Landers et al. |
| 2009/0099041 A1 | 4/2009 | Church et al. |
| 2009/0105081 A1 | 4/2009 | Rodesch |
| 2009/0119313 A1 | 5/2009 | Pearce |
| 2009/0127589 A1 | 5/2009 | Rothberg et al. |
| 2009/0129647 A1 | 5/2009 | Dimitrova et al. |
| 2009/0156412 A1 | 6/2009 | Boyce, IV et al. |
| 2009/0163366 A1 | 6/2009 | Nickerson et al. |
| 2009/0191565 A1 | 7/2009 | Lapidus et al. |
| 2009/0192047 A1 | 7/2009 | Parr et al. |
| 2009/0203014 A1 | 8/2009 | Wu et al. |
| 2009/0226975 A1 | 9/2009 | Sabot et al. |
| 2009/0233814 A1 | 9/2009 | Bashkirov et al. |
| 2009/0298064 A1 | 12/2009 | Batzoglou et al. |
| 2009/0318310 A1 | 12/2009 | Liu et al. |
| 2010/0035243 A1 | 2/2010 | Muller et al. |
| 2010/0035252 A1 | 2/2010 | Rothberg et al. |
| 2010/0063742 A1 | 3/2010 | Hart et al. |
| 2010/0069263 A1 | 3/2010 | Shendure et al. |
| 2010/0105107 A1 | 4/2010 | Hildebrand et al. |
| 2010/0137143 A1 | 6/2010 | Rothberg et al. |
| 2010/0137163 A1 | 6/2010 | Link et al. |
| 2010/0188073 A1 | 7/2010 | Rothberg et al. |
| 2010/0197507 A1 | 8/2010 | Rothberg et al. |
| 2010/0216151 A1 | 8/2010 | Lapidus et al. |
| 2010/0248984 A1 | 9/2010 | Shaffer et al. |

(56) References Cited

U.S. PATENT DOCUMENTS

| | | |
|---|---|---|
| 2010/0282617 A1 | 11/2010 | Rothberg et al. |
| 2010/0285578 A1 | 11/2010 | Selden et al. |
| 2010/0297626 A1 | 11/2010 | McKernan et al. |
| 2010/0300559 A1 | 12/2010 | Schultz et al. |
| 2010/0300895 A1 | 12/2010 | Nobile et al. |
| 2010/0301042 A1 | 12/2010 | Kahlert |
| 2010/0301398 A1 | 12/2010 | Rothberg et al. |
| 2010/0304982 A1 | 12/2010 | Hinz et al. |
| 2010/0330619 A1 | 12/2010 | Willis et al. |
| 2011/0004413 A1 | 1/2011 | Carnevali et al. |
| 2011/0009278 A1 | 1/2011 | Kain et al. |
| 2011/0015863 A1 | 1/2011 | Pevzner et al. |
| 2011/0021366 A1 | 1/2011 | Chinitz et al. |
| 2011/0034342 A1 | 2/2011 | Fox |
| 2011/0098193 A1 | 4/2011 | Kingsmore et al. |
| 2011/0159499 A1* | 6/2011 | Hindson et al. ............ 435/6.12 |
| 2011/0166029 A1 | 7/2011 | Margulies et al. |
| 2011/0230365 A1 | 9/2011 | Rohlfs et al. |
| 2011/0257889 A1 | 10/2011 | Klammer et al. |
| 2011/0301042 A1 | 12/2011 | Steinmann et al. |
| 2012/0015050 A1 | 1/2012 | Abkevich et al. |
| 2012/0021930 A1* | 1/2012 | Schoen et al. .................... 506/9 |
| 2012/0059594 A1 | 3/2012 | Hatchwell et al. |
| 2012/0165202 A1 | 6/2012 | Porreca et al. |
| 2012/0179384 A1 | 7/2012 | Kuramitsu et al. |
| 2012/0252020 A1 | 10/2012 | Shuber |
| 2012/0252684 A1 | 10/2012 | Selifonov et al. |
| 2013/0275103 A1 | 10/2013 | Struble et al. |
| 2013/0344096 A1 | 12/2013 | Chiang et al. |

FOREIGN PATENT DOCUMENTS

| | | | |
|---|---|---|---|
| EP | 2437191 | A2 | 4/2012 |
| WO | 1995/011995 | A1 | 5/1995 |
| WO | 1996/019586 | A1 | 6/1996 |
| WO | 1998/014275 | A1 | 4/1998 |
| WO | 1998/044151 | A1 | 10/1998 |
| WO | 2000/018957 | A1 | 4/2000 |
| WO | 2002093453 | A2 | 11/2002 |
| WO | 2004/018497 | | 3/2004 |
| WO | 2004/083819 | A2 | 9/2004 |
| WO | 2005/003304 | A1 | 1/2005 |
| WO | 2007/010251 | A2 | 1/2007 |
| WO | 2007/107717 | A1 | 9/2007 |
| WO | 2007/123744 | | 11/2007 |
| WO | 2007/135368 | A2 | 11/2007 |
| WO | 2009/036525 | A2 | 3/2009 |
| WO | 2010024894 | A1 | 3/2010 |
| WO | 2010126614 | A2 | 11/2010 |
| WO | 2011066476 | A1 | 6/2011 |
| WO | 2011067378 | A1 | 6/2011 |
| WO | 2012040387 | A1 | 3/2012 |
| WO | 2012/051208 | A2 | 4/2012 |
| WO | 2012/087736 | A1 | 6/2012 |
| WO | 2012/109500 | A2 | 8/2012 |
| WO | 2012/134884 | A1 | 10/2012 |
| WO | 2013/058907 | A1 | 4/2013 |

OTHER PUBLICATIONS

Mamanova et al. (Nat. Meth., 2007, 7(2):111-118).*
Wahl et al. (Proc. Natl. Acad. Sci., 1979, 76:3683-3687).*
Deng et al. (Nature, 2009, 27:353-360).*
Hardenbol et al. "Highly multiplexed molecular inversion probe genotyping: over 10,000 targeted SNPs genotyped in a single tube assay" 2005 Genome Res 15:269-75.
Porreca et al. Multiplex Amplification of Large Sets of Human Exons, 2007 Nat. Methods 4:931-6.
Krishnakumar et al. "A comprehensive assay for targeted multiplex amplification of human DNA sequences" 2008 Proc Natl Acad Sci USA 105:9296-301.
Turner et al., "Methods for Genomic Partioning" Annu. Rev. Genomics Hum. Genet. 2009 10:263-84.
Turner EH, et al. "Massively Parallel Exon Capture and Library-free resequencing across 16 individuals" Nat Methods. Apr. 6, 2009:1-2.
Summerer, "Enabling Technologies of Genomic-scale Sequence Enrichment for Targeted High-Throughput Sequencing", Genomics 94 (2009) 363-368.
Mamanova et al. "Target-enrichment strategies for next-generation sequencing" Nature Methods, vol. 7, No. 2 pp. 111-118 (2010).
Ng. et al. "Targeted Capture and Massively Parallel Sequencing of Twelve Human Exomes" Nature. Sep. 10, 2009; 461(7261): 272-276.
International Search Report and Written Opinion for PCT/US2013/036575 dated Aug. 12, 2013, 10 pages.
Thompson, et al., 2011, The properties and applications of single-molecule DNA sequencing, Genome Biology 12(2):217, 10 pages.
Australian Patent Examination Report No. 1 dated Aug. 12, 2014, for Australian Patent Application No. 2010242073 filed Apr. 30, 2010, 4 pages.
International Search Report and Written Opinion dated Sep. 3, 2014 for International Patent Application No. PCT/US14/27324, filed Mar. 14, 2014 (8 pages).
Supplementary European Search Report dated Aug. 26, 2014, for European Patent Application No. 12765217.0, filed Mar. 20, 2012, 5 pages.
Smirnov, et al., 1996, Sequencing oligonucleotides by exonuclease digestion and delayed extraction matrix-assisted laser desorption ionization time-of-flight mass spectrometry, Anal Biochem 238(1):19-25.
Extended European Search Report dated Feb. 29, 2016 for European Patent Application No. 13778619.0 (10 Pages).
Nicholas, H. B. Jr., et al., 2002, Strategies for multiple sequence alignment, Biotechniques 32:572-91.
Nickerson, et al., 1990, Automated DNA diagnostics using an ELISA-based oligonucleotide ligation assay, Proc. National Academy of Science 87:8923-7.
Nielsen, et al., 1999, Peptide Nucleic Acids, Protocols and Applications (Norfolk: Horizon Scientific Press, 1-19).
Nilsson, et al., 2006, Analyzing genes using closing and replicating circles, Trends in Biotechnology 24:83-8.
Ning, Z., et al., 2001, SSAHA: a fast search method for large DNA databases, Genome Research 11(10): 1725-9 (2001).
Nordhoff, et al.; 2003, Ion stability of nucleic acids in infrared matrix-assisted laser desorption/ionization mass spectrometry, Nucleic Acids Research 21(15):3347-57.
Oefner, et al., 1996, Efficient random subcloning of DNA sheared in a recirculating point-sink flow system, Nucleic Acids Research 24:3879-89.
Oka, et al., 2006, Detection of Loss of Heterozygosity in the p53 Gene in Renal Cell Carcinoma and Bladder Cancer Using the Polymerase Chain Reaction, Molecular Carcinogenesis 4(1).
Oliphant, et al., 2002, BeadArray?Technology: Enabling an Accurate, Cost-Effective Approach to High-Throughput Genotyping, Biotechniques Suppl:56-8, 60-1.
Ordahl, et al., 1976, Sheared DNA fragment sizing:comparison of techniques, Nucleic Acids Research 3:2985-99.
Ostrer, et al., 2001, A genetic profile of contemporary Jewish populations, Nature Reviews Cancer 2:891-8.
Owens, et al., 1998, Aspects of oligonucleotide and peptide sequencing with MALDI and electrospray mass spectrometry, Bioorg Med Chem 6:1547-1554.
Parameswaran, et al., 2007, A pyrosequencing-tailored nucleotide barcode design unveils opportunities for large-scale sample multiplexing, Nucleic Acids Research 35:e130, pp. 1-9.
Pearson W.R., et al., 1988, Improved tools for biological sequence comparison, PNAS 85(8):2444-8.
Pertea, et al., 2003, TIGR gene indices clustering tools (TGICL), Bioinformatics 19(5):651-52.
Pieles, et al., 1993, Matrix-assisted laser desorption ionization time-of-flight mass spectrometry: A powerful tool for the mass and sequence analysis of natural and modified oligonucleotides, Nucleic Acids Res 21:3191-3196.
Procter, et al., 2006, Molecular Diagnosis of Prader—Willi and Angelman Syndromes by Methylation-Specific Melting Analysis

(56) References Cited

OTHER PUBLICATIONS and Methylation-Specific Multiplex Ligation-Dependent Probe Amplification, Clinical Chemistry 52(7):1276-83.
Quail, et al., 2010, DNA: Mechanical Breakage, Encyclopedia of Life Sciences 2010.
Rambaut, et al., 1997, Seq-Gen:an application for the Monte Carlo simulation of DNA sequence evolution along phylogenetic trees, Bioinformatics (formerly CABIOS) 13:235-38.
Richter, et al., 2008, MetaSim—A Sequencing Simulator for Genomics and Metagenomics, PLOS ONE 3:e3373.
Roberts, R.J., 1980, Restriction and modification enzymes and their recognition sequence, Nucleic Acids Research 8 (1):r63-r80.
Rosendahl, et al., 2013, CFTR, SPINK1, CTRC and PRSS1 variants in chronic pancreatitis: is the role of mutated CFTR over estimated?, Gut 62:585-92.
Rothberg, et al., 2011, An integrated semiconductor device enablingnon-optical genome sequencing, Nature 475:348-52.
Rowntree, et al., 2003, The Phenotypic Consequences of CFTR Mutations, Annals of Human Genetics 67:471-85.
Sanger, et al., 1977, DNA sequencing with chain-terminating inhibitors, Proc.National Academy of Science USA 74 (12):5463-7.
Santa Lucia, John Jr., 1998, A unified view of polymer, dumbbell, and oligonucleotide DNA nearest-neighbor thermodynamics, Proc. National Academy of Science USA 95:1460-5.
Sargent, T.D., 1988, Isolation of Differentially Expressed Genes, Methods in Enzymology 152:432.
Sauro, 2004, How Do You Calculate a Z-Score/ Sigma Level?, https://www.measuringusability.com/zcalc.htm (online publication).
Sauro, 2004, What's a Z-Score and Why Use it in Usability Testing?, https://www.measuringusability.com/z.htm (online publication).
Schadt, et al., 2010, A window into third-generation sequencing, Human Molecular Genetics 19(R2):R227-40.
Schatz, et al., 2010, Assembly of large genomes using second-generation sequencing, Genome Res., 20:1165-1173.
Schrijver, et al., 2005, Diagnostic Testing by CFTR Gene Mutation Analysis in a Large Group of Hispanics, The Journal of Molecular Diagnostics 7:289-99.
Schuette, et al., 1995, Sequence analysis of phosphorothioate oligonucleotides via matrix-assisted laser desorption ionization time-of-flight mass spectrometry, J. Pharm. Biomed. Anal 13:1195-1203.
Schwartz, et al., 2009, Identification of Cystic Fibrosis Variants by Polymerase Chain Reaction/Oligonucleotide Ligation Assay, The Journal of Molecular Diagnostics 11(3):211-15.
Schwartz, Stuart, 2011, Clinical Utility of Single Nucleotide Polymorphism Arrays, Clinics in Laboratory Medicine 31 (4):581-94.
Sequeira, et al., 1997, Implementing generic, object-oriented models in biology, Ecological Modeling 94.1:17-31.
Sievers F., et al., 2011, Fast, scalable generation of high-quality protein multiple sequence alignments using Clustal Omega, Mol Syst Biol 7:539.
Simpson, J.T., et al., 2009, ABySS: A parallel assembler for short read sequence data, Genome Res., 19(6): 1117-23.
Slater, G., & Birney, E, 2005, Automated generation of heuristics for biological sequence comparison, BMC Bioinformatics 6:31.
Soni, G. V., & Meller, A, 2007, Progress toward ultrafast DNA sequencing using solid-state nanopores, Clin Chem 53: 1996-2001.
Spanu, P.D., et al., 2010, Genome expansion and gene loss in powdery mildew fungi reveal tradeoffs in extreme parasitism, Science 330(6010): 1543-46.
Sunnucks, et al., 1996, Microsatellite and Chromosome Evolution of Parthenogenetic Sitobion Aphids in Australia, Genetics Society of America 144:747-56.
Thauvin-Robinet, et al., 2009, The very low penetrance of cystic fibrosis for the R117H mutation: a reappraisal for genetic counselling and newborn screening, Journal of Medical Genetics 46:752-8.

Thompson, et al., 1994, Clustal W: improving the sensitivity of progressive multiple sequence alignment through sequence weighting, position-specific gap penalities and matrix choice, Nucl. Acids. Res., 22:4673-80.
Thorstenson, et al., 1998, An Automated Hydrodynamic Process for Controlled, Unbiased DNA Shearing, Genome Methods 8:848-55.
Thorvaldsdottir, et al., 2012, Integrative GenomicsViewer (IGV): high-performance genomics data visualization and exploration, Briefings in Bioinformatics 24(2):178-92.
Tokino, 1996, Characterization of the human p57 KIP2 gene: alternative splicing, insertion/deletion polymorphisms in VNTR sequences in the coding region, and mutational analysis, Human Genetics 96:625-31.
Wallace, et al., 1979, Hybridization of synthetic oligodeoxyribonucteotides to dp x 174DNA:the effect of single base pair mismatch, Nucleic Acids Research 6:3543-3557.
Warner, et al., 1996, A general method for the detection of large CAG repeat expansions by fluorescent PCR, Journal Medical Genetics 33(12):1022-6.
Warren, R., et al., 2007, Assembling millions of short DNA sequences using SSAKE, Bioinformatics, 23:500-501.
Watson, et al., 2004, Cystic fibrosis population carrier screening: 2004 revision of American College of Medical Genetics mutation panel, Genetics in Medicine 6(5).
Williams , 2003, Restriction Endonucleases Classification, Properties, and Applications, Molecular Biotechnology 23 (3):225-43.
Wittung, et al., 1997, Extended DNA-Recognition Repertoire of Peptide Nucleic Acid (PNA): PNA-dsDNA Triplex Formed with Cytosine-Rich Homopyrimidine PNA, Biochemistry 36:7973.
Wu & Aboleneed , 2001, Improved oligonucleotide sequencing by alkaline phosphatase and exonuclease digestions with mass spectrometry, Anal Biochem 290:347-352.
Wu, et al., 1998, Sequencing regular and labeled oligonucleotides using enzymatic digestion and ionspray mass spectrometry, Anal Biochem 263:129-138.
Yau, et al., 1996, Accurate diagnosis of carriers of deletions and duplications in Duchenne/Becker muscular dystrophy by fluorescent dosage analysis, Journal Medical Genetics 33(7):550-8.
Yoo, et al., 2009, Applications of DNA Microarray in Disease Diagnostics, Journal of Microbiology and Biotechnology 19(7):635-46.
Yoshida, et al., 2004, Role of BRCA1 and BRCA2 as regulators of DNA repair, transcription, and cell cycle in response to DNA damage, Cancer Science 95(11)866-71.
Yu, 2007, A Novel Set of DNA Methylation Markers in Urine Sediments for Sensitive/Specific Detection of Bladder Cancer, Clinical Cancer Research 13(24):7296-7304.
Yuan, Robert, 1981, Structure and Mechanism of Multifunctional Restriction Endonucleases Annuual Review of Biochemistry 50:285-319.
Zerbino D.R., et al., 2008, Velvet: algorithms for de novo short read assembly using de Bruijn graphs, Genome Research 18 (5):821-829.
Zhang, et al., 2011, Is Mitochondrial tRNAphe Variant m.593T.Ca Synergistically Pathogenic Mutation in Chinese LHON Families with m.11778G.A? PLOS ONE 6(10):e26511.
Zhao F., et al., 2009, PGA4genomics for comparative genome assembly based on genetic algorithm optimization, Genomics. 94(4):284-6.
Zheng, et al., 2011, iAssembler: a package for de novo assembly of Roche-454/Sanger transcriptome sequences, BMC Bioinformatics 12:453.
Zimmerman, et al., 2010, A novel custom resequencing array for dilated cardiomyopathy, Genetics in Medicine 12 (5):268-78.
Alazard, et al., 2005, Sequencing Oligonucleotides by Enrichment of Coupling Failures Using Matrix-Assisted Laser Desorption/ Ionization Time-of-Flight Mass Spectrometry, Current Protocols in Nucleic Acid Chemistry 10.10.1-10.10.7.
Akhras, M.S., et al., 2007, Connector Inversion Probe Technology: A Powerful OnePrimer Multiplex DNA Amplification System for Numerous Scientific Applications PLOS ONE 2(9):e915.
Alazard, et al., 2002, Sequencing of production-scale synthetic oligonucleotides by enriching for coupling failures using matrix-

(56) References Cited

OTHER PUBLICATIONS assisted laser desorption/ ionization time-of-flight mass spectrometry, Analytical biochemistry 301:57-64.
Albert, 2007, Direct selection of human genomic loci by microarray hybridization, Nature Methods 4(11):903-5.
Aljanabi, Salah M.; Martinez, Iciar, 1997, Universal and rapid salt-extraction of high quality genomic DNA for PCR-based techniques Nucl. Acids Res. 25:4692-3.
Antonarakis & the Nomenclature Working Group, 1998, Recommendations for a nomenclature system for human gene mutations, Human Mutation 11:1-3.
Ball, M.P., et al., 2009, Targeted and genome-scale strategies reveal gene-body methylation signatures in human cells, Nature Biotechnology, 27:361-8.
Barany, F, 1991, Genetic disease detection and DNA amplification using cloned thermostable ligase, PNAS, 88:189-193.
Barany, F, 1991, The Ligase Chain Reaction in a PCR World, Genome Research, 1:5-16.
Bau, et al., 2008, Targeted next-generation sequencing by specific capture of multiple genomic loci using low-volume microfluidic DNA arrays, Analytical and bioanalytical chem 393(1):171-5.
Benner, et al., 2001, Evolution, language and analogy in functional genomics, Trends in Genetics 17:414-8.
Bentzley, et al., 1996, Oligonucleotide sequence and composition determined by matrix-assisted laser desorption/ ionization, Anal Chem 68:2141-2146.
Bentzley, et al., 1998, Base specificity of oligonucleotide digestion by calf spleen phosphodiesterase with matrixassisted laser desorption ionization analysis, Anal Biochem 258:31-37.
Bickle, Thomas A. & Kruger, Detlev, H., 1993, Biology of DNA Restriction, Microbiological Reviews 57(2):434-50.
Boyer, H. W., 1971, DNA restriction and modification mechanisms in bacteria, Annual Review of Microbiology 25:153-76.
Braasch, et al., 2001, Locked nucleic acid (LNA): ¢ne-tuning the recognition of DNA and RNA, Chemistry & Biology 8 (1):1-7.
Braslaysky, et al., 2003, Sequence information can be obtained from single DNA molecules, Proceedings of the National Academy of Sciences, (USA) 100:3960-4.
Brown, et al., 1979, Chemical synthesis and cloning of a tyrosine tRNA gene, Methods Enzymol., 68:109.
Browne, Kenneth A., 2002, Metal ion-catalyzed nucleic acid alkylation and fragmentation, Journal of American Chemical Society, 124(27)7950-62.
Bunyan, et al., 2004, Dosage analysis of cancer predisposition genes by multiplex ligation-dependent probe amplification, British Journal of Cancer, 91(6):1155-59.
Burrow & Wheeler, 1994, A block-sorting lossless data compression algorithm, Technical Report 124, Digital Equipment Corporation, CA.
Castellani, et al., 2008, Consensus on the use and interpretation of cystic fibrosis mutation analysis in clinical practice, Journal of Cystic Fibrosis 7(3):179-96.
Chan, et al., 2011, Natural and engineered nicking endonucleases from cleavage mechanism to engineering of strand-specificity, Nucleic Acids Research, 39(1):1-18.
Chevreux, B., et al., 1999, Genome Sequence Assembly Using Trace Signals and Additional Sequence Information, Computer Science and Biology: Proceedings of the German Conference on Bioinformatics (GCB) 99:45-56.
Chirgwin, et al., 1979, Isolation of biologically active ribonucleic acid from sources enriched in ribonuclease, Biochemistry, 18:5294-99.
Choe, et al., 2010, Novel CFTR Mutations in a Korean Infant with Cystic Fibrosis and Pancreatic Insufficiency, J Korean Med Sci 25:163-5.
Ciotti, et al., 2004, Triplet Repeat Primed PCR (TP PCR) in Molecular Diagnostic Testing for Friedrich Ataxia, Journal of Molecular Diagnostics 6(4):285-9.
Collins, et al., 2004, Finishing the euchromatic sequence of the human genome, Nature 431.7011:931-45.
Dahl, et al., 2005, Multiplexamplification enabled by selective circularization of large sets of genomic DNA fragments, Nucleic Acids Research 33:e71.
de la Bastide, M. & McCombie, 2007, W. R., Assembling genome DNA sequences with PHRAP, Current Protocols in Bioinformatics, 17:11.4.1-11.4.15.
Delcher, A.L., et al., 1999, Alignment of whole genomes, Nucleic Acids Research, 27:11.
Deng, et al., 2009, Targeted bisulfite sequencing reveals changes in DNA methylation associated with nuclear reprogramming, nature biotechnology 27:353-60 (and supplement).
DiGuistini, S., et al., 2009, De novo genome sequence assembly of a filamentous fungus using Sanger, 454 and Illumina sequence data, Genome Biology, 10:R94.
Dong, C. & Yu, B., 2011, Mutation Surveyor: An In Silico Tool for Sequencing Analysis, Methods in Molecular Biology 760:223-37.
Dore, et al., 1969, The Alkaline Denaturation of DNA, Biophysical Journal 9(11):1281-1311.
Dudley, et al., 2009, A Quick Guide for Developing Effective Bioinformatics Programming Skills, PLOS Comput Biol 5 (12):e1000589.
European Search Report for EP application No. 10770071.8, dated Nov. 8, 2012.
Exam Report from EPO for EP 10770071.8, dated Jul. 16, 2013.
Faulstich, et al., 1997, A sequencing method for RNA oligonucleotides based on mass spectrometry, Anal Chem 69:4349-4353.
Fares, et al., 2008, Carrier frequency of autosomal-recessive disorders in the Ashkenazi Jewish population: should the rationale for mutation choice for screening be reevaluated?, Prenatal Diagnosis 28:236-41.
Frey, Bruce, 2006, Statistics Hacks 108-115.
Friedenson, 2005, BRCA1 and BRCA2 Pathways and the Risk of Cancers Other Than Breast or Ovarian, Medscape General Medicine 7(2):60.
Gemayel, et al., 2010, Variable Tandem Repeats Accelerate Evolution of Coding and Regulatory Sequences, Annual Review of Genetics 44:445-77.
Glover, et al., 1995, Sequencing of oligonucleotides using high performance liquid chromatography and electrospray mass spectrometry, Rapid Corn Mass Spec 9:897-901.
Gnirke, et al., 2009, Solution hybrid selection with ultra-long oligonucleotides for massively parallel targeted sequencing, nature biotechnology 27:182-9.
Goto, et al., 2010, BioRuby: bioinformatics software for the Ruby programming language, Bioinformatics 26 (20):2617-9.
Gut, I. G. & Beck, S., 1995, A procedure for selective DNA alkylation and detection by mass spectrometry, Nucleic Acids Research 23(8):12367-73.
Hammond, et al., 1996, Extraction of DNA from Preserved Animal Specimens for Use in Randomly Amplified Polymorphic DNA Analysis, Analytical Biochemistry 240:298-300.
Hardenbol, et al., 2005, Highly multiplexed molecular inversion probe genotyping: Over 10,000 targeted SNPs genotyped in a single tube assay, Genome Research 15:269-75.
Harris, et al., 2006, Defects Can Increase the Melting Temperature of DNA-Nanoparticle Assemblies, The Journal of Physical Chemistry B 110:16393-6.
Harris, et al., 2008, Single-Molecule DNA Sequencing of a Viral Genome, Science 320:106-9.
Hodges, et al., 2007, Genome-wide in situ exon capture for selective resequencing, nature genetics 29:1522-7.
Holland, et al., 2008, BioJava: an open-source framework for bioinformatics, Bioinformatics 24(18):2096-97.
Huang, et al., 2008, Comparative analysis of common CFTRpolymorphisms poly-T, TGrepeats and M470V in a healthy Chinese population, World J Gastroenterol 14(12):1925-30.
Husemann, P. & Stoye, 2009, Phylogenetic Comparative Assembly, Algorithms in Bioinformatics: 9th International Workshop, pp. 145-156, Salzberg, S., and Warnow, T., Eds. Springer-Verlag, Berlin Heidelberg.
International Preliminary Report on Patentability for PCT/US2010/01293, dated Oct. 28, 2010.

(56) References Cited

OTHER PUBLICATIONS

International Search Report and Written Opinion for WO2010/126614.
International Search Report and Written Opinion dated Apr. 3, 2012, for International Patent Application No. PCT/US2011/065098, filed Dec. 15, 2011 (8 pages).
International Search Report and Written Opinion dated Aug. 12, 2013, for International Patent Application No. PCT/US13/36575, filed Apr. 15, 2013 (9 pages).
International Search Report and Written Opinion dated Feb. 25, 2013 for International Patent Application No. PCT/US12/55362.
International Search Report and Written Opinion dated Jun. 10, 2013, for International Patent Application No. PCT/US13/33435, filed Mar. 22, 2013 (6 pages).
International Search Report and Written Opinion dated Jun. 14, 2012, for International Patent Application No. PCT/US12/29790, filed Mar. 20, 2012 (8 pages).
International Search Report and Written Opinion dated Nov. 1, 2013, for International Patent Application No. PCT/US2013/044039, filed Jun. 4, 2013 (6 pages).
International Search Report and Written Opinion dated Feb. 4, 2014, for Patent Application No. PCT/US13/62842, filed Oct. 1, 2013 (5 pages).
International Search Report and Written Opinion dated Jun. 28, 2013, for Patent Application No. PCT/US2013/032885, filed Mar. 19, 2013 (9 pages).
International Search Report and Written Opinion dated Oct. 28, 2010, for Patent Application No. PCT/US2010/001293, filed Apr. 30, 2010 (8 pages).
Iqbal, et al., 2012, De novo assembly and genotyping of variants using colored de Bruijn graphs, Nature Genetics, 44 (2):226-233.
Jaijo, et al., 2010, Microarray-Based Mutation Analysis of 183 Spanish Families with Usher Syndrome, Investigative Ophthalmology & Visual Science 51(3):1311-7.
Jones, et al., 2008, Core Signaling Pathways in Human Pancreatic Cancers Revealed by Global Genomic Analyses, Science 321(5897):1801-1806.
Kent, W.J., 2002, BLAT-The BLAST-like alignment tool, Genome Research 4: 656-664.
Kircher, et al., 2010, High-throuhput DNA sequencing—concepts and limitations, Bioassays 32:524-36.
Kirpekar, et al., 1994, Matrix assisted laser desorption/ionization mass spectrometry of enzymatically synthesized RNA up to 150 kDa, Nucleic Acids Res 22:3866-3870.
Klein, et al., 2011, LOCAS—a low coverage assembly tool for resequence projects, PLoS One vol. 6, Issue 8, Document e23455, Aug. 15, 2011 (10 pages).
Krawitz, et al., 2010, Microindel detection in short-read sequence data, Bioinformatics 26(6).
Kreindler, J. L., 2010, Cystic fibrosis: Exploiting its genetic basis in the hunt for new therapies, Pharmacology and Therapeutics 125(2):219-29.
Kumar, S., et al., 2010, Comparing de novo assemblers for 454 transcriptome data, Genomics 11:571.
Kurtz, S., et al., 2004, Versatile and open software for comparing large genomes, Genome Biology, 5:R12.
Lam, et al., 2008, Compressed indexing and local alignment of DNA, Bioinformatics 24(6):791-97.
Langmead, et al., 2009, Ultrafast and memory-efficient alignment of short DNA sequences to the human genome, Genome Biology, 10:R25.
Larkin M.A., et al., 2007, Clustal W and Clustal X version 2.0, Bioinformatics, 23, 2947-2948.
Lecompte, O., et al., 2001, Multiple alignment of complete sequences (MACS) in the post-genomic era, Gene 270:17-30.
Li H. & Durbin R., 2009, Fast and accurate short read alignment with Burrows-Wheeler transform, Bioinformatics, 25 (14):1754-60.
Li H. & Durbin R., 2010, (2010) Fast and accurate long-read alignment with Burrows-Wheeler Transform. Bioinformatics, Epub.
Li, et al., 2008, SOAP: short oligonucleotide alignment program, Bioinformatics 24(5):713-14.
Li, et al., 2009, SOAP2: an improved ultrafast tool for short read alignment, Bioinformatics 25(15): 1966-67.
Li, et al., 2009, The Sequence Alignment/Map format and SAMtools, Bioinformatics, 2009, 25(16):2078-9.
Li, et al., 2011, Single Nucleotide Polymorphism Genotyping and Point Mutation Detection by Ligation on Microarrays, Journal of Nanoscience and Nanotechnology 11(2):994-1003.
Lin, et al., 2012, Development and evaluation of a reverse dot blot assay for the simultaneous detection of common alpha and beta thalassemia in Chinese, Blood Cells Molecules, and Diseases 48(2):86-90.
Lipman, D.J., et al., 1985, Rapid and sensitive protein similarity searches, Science 227(4693):1435-41.
Margulies, et al., 2005, Genome sequencing in microfabricated high-density picolitre reactors, Nature 437:376-380.
Marras, 1999, Multiplex detection of single-nucleotide variations using molecular beacons, Genetic Analysis: Biomolecular Engineering 14:151.
Maxam, et al., 1977, A new method for sequencing DNA, Proc. of National Academy of Science USA 74:560-4.
May, Robert M., 1988, How Many Species Are There on Earth?, Science 241:1441.
Mills, R.E., et al., 2010, Mapping copy number variation by population-scale genome sequencing, Nature 470:59-65.
Minton, et al., 2011, Mutation Surveyor: Software for DNA Sequence Analysis, Methods in Molecular Biology 688:143-53.
Mockler, et al., 2005, Applications of DNA tiling arrays for whole-genome analysis, Genomics 85:1-15.
Moudrianakis E. N. & Beer M., 1965, Base sequence determination in nucleic acids with the electron microscope, PNAS, 53:564-71.
Mullan, L. J., 2002, Multiple sequence alignment-the gateway to further analysis, Brief Bioinform., 3:303-5.
Nan, et al., 2006, A novel CFTR mutation found in a Chinese patient with cystic fibrosis, Chinese Medical Journal 119 (2):103-9.
Narang, et al., 1979, Improved phosphotriester method for the synthesis of gene fragments, Methods Enzymol., 68:90.
Ng, et al., 2009, Targeted capture and massively parallel sequencing of 12 human exomes, Nature 461(7261):272-6.

\* cited by examiner

CAPTURE REACTIONS

RELATED APPLICATION

The present patent application claims the benefit of and priority to U.S. Provisional Patent Application Ser. No. 61/624,778 filed on Apr. 16, 2012, the entirety of which is herein incorporated by reference.

FIELD OF INVENTION

The invention generally relates to methods for improving performance of capture reactions.

BACKGROUND

Routine sequencing of whole genomes is not economically feasible, and as an alternative, it is often necessary to select genomic areas of interest for capture prior to sequencing. Numerous techniques have been developed for capturing target nucleic acids for subsequent detection and analysis that are compatible for use with massively parallel sequencing platforms. Such exemplary techniques include multiplex PCR capture with primer pairs and array-based or solution-based hybrid capture. Often, capture-based technologies are designed to provide a mechanism to analyze complex genomes by selecting genomic areas of interest prior to sequencing or detection. By analyzing the area of interest, the genome can be studied with significantly reduced costs and reduced time as compared with the task of sequencing large numbers of complex genomes in their entireties.

A problem with nucleic acid capture techniques is their inability to capture multiple loci with substantially uniform efficiencies. Such efficiencies define the amount of sequencing required to adequately cover the targets. Turner et al., Annu. Rev. Genomics Hum. Genet. 2009 10:263-84. Generally, the distribution of abundances of capture reaction products is rather wide, with the most and least frequent species spanning multiple orders of magnitude. Such a wide distribution in abundance means that a large number of sequencing reactions must be performed to generate an effective coverage of the target, increasing costs and time to results.

SUMMARY

The invention recognizes that capture reactions performed on whole genomic nucleic acids result in poor uniformity due to, for example, the folding and melting temperature of high molecular weight genomic nucleic acids. The massive length of genomic nucleic acids in base pairs, approximately $3.3 \times 10^9$ bp for humans, and the natural folding of genomic nucleic acids prohibit the ability of capture moieties introduced to the genomic nucleic acid from being exposed to the targets for hybridization, leading to failed or inefficient capture of the target.

The invention further recognizes that fragmenting nucleic acid prior to performing a capture reaction allows for greater exposure of a target site to a capture moiety, reducing failed capture, and increasing the percentage of capture moieties that hybridize to targets within the genome. Accordingly, methods of the invention lead to a product that is substantially more uniform than products obtained from capture reactions in which a fragmenting step has not been performed prior to the capture reaction. This advantageously yields a target abundance distribution that is significantly more uniform than if a native high molecular weight genomic nucleic acid is used. Such products are more suited for use in a number of applications, particularly in clinical diagnostics.

In certain aspects, methods of the invention involve obtaining a nucleic acid, fragmenting the nucleic acid into nucleic acid fragments, and capturing a target on a nucleic acid fragment. Methods of the invention work well with any capture technique and are particularly suited for capture techniques using molecular inversion probes. The nucleic acid can be genomic DNA, genomic RNA, or a whole genome amplification (WGA) product. Performance of the method with a WGA product is useful in situations where input DNA is limiting, e.g. limiting amounts of tumor tissue, fetal cells circulating in maternal blood, etc.

In embodiments that utilize molecular inversion probes (MIP), any molecular inversion probe may be used. An exemplary MIP is a single-stranded probe about 70 nucleotides in length, composed of a universal core of 30 nucleotides that is flanked by specific 20-nucleotide targeting sequences on each side, i.e. targeting arms. However, the length and composition of the probe can vary to most adequately capture the desired target sequence. The targeting arms are designed to hybridize to specific genomic regions upstream and downstream of a target sequence of interest located on the nucleic acid fragment. After the target sequence of interest is isolated between the target arms, the target sequence can be analyzed. Although each MIP captures one target of interest for analysis, multiple probes can be combined into a single vessel containing the fragmented nucleic acids for a multiplexed assay that simultaneously examines multiple target loci.

Fragmenting the nucleic acid can be accomplished by any technique known in the art. Exemplary techniques include mechanically fragmenting, chemically fragmenting, and/or enzymatically fragmenting. Mechanical nucleic acid fragmentation can be, for example, sonication, nebulization, and hydro-shearing (e.g., point-sink shearing). Enzymatic nucleic acid fragmenting includes, for example, use of nicking endonucleases or restriction endonucleases. The nucleic acid can also be chemically fragmented by performing acid hydrolysis on the nucleic acid or treating of the nucleic acid with alkali or other reagents.

The fragment length can be adjusted based on the sizes of the nucleic acid targets to be captured. The nucleic acid fragments can be of uniform length or of a distribution of lengths. In certain embodiments, the nucleic acid is fragmented into nucleic acid fragments having a length of about 10 kb or 20 kb. In addition, the nucleic acid fragments can range from between 1 kb to 20 kb, with various distributions.

In certain embodiments, the nucleic acid is also denatured, which may occur prior to, during, or after the fragmenting step. The nucleic acid can be denatured using any means known in the art, such as pH-based denaturing, heat-based denaturing, formamide or urea, exonuclease degradation, or endonuclease nicking. In certain embodiments, the use of pH, such as in acid hydrolysis, alone or in combination with heat fragments and either partially or fully denatures the nucleic acid. This combined fragmenting and denaturing method can be used to fragment the nucleic acid for MIP capture or to fragment captured target nucleic acids or whole genomic DNA for shotgun library preparation.

DETAILED DESCRIPTION

Figure 1:
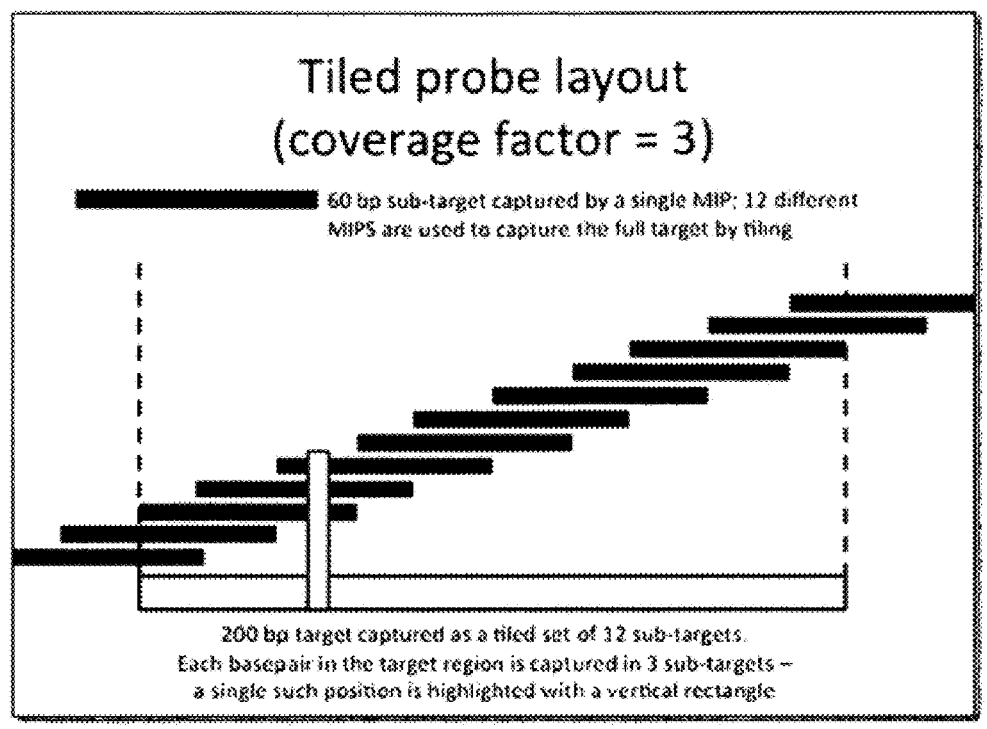
FIG. 1 illustrates a non-limiting embodiment of a tiled probe layout.

This invention generally relates to improving performance of molecular inversion probe capture reactions. In certain embodiments, methods of the invention include the steps of obtaining a genomic nucleic acid, fragmenting the genomic nucleic acid, optionally denaturing the genomic nucleic acid or fragmented genomic nucleic acid, and performing a capture reaction on the fragmented genomic nucleic acid. Methods of the invention work well with any capture technique and are particularly suited for capture techniques using molecular inversion probes. Fragmenting genomic nucleic acids prior to performing capture advantageously improves the uniformity of the product of the capture reaction.

Nucleic acids suitable for use in aspects of the invention include but are not limited to genomic DNA, genomic RNA, synthesized nucleic acids, whole or partial genome amplification product, and high molecular weight nucleic acids, e.g. individual chromosomes. Genomic DNA and genomic RNA constitute the total genetic information of an organism. Genomic nucleic acids molecules are generally large, and in most organisms are organized into DNA-protein complexes called chromosomes, which the exception of viruses that have RNA genomes. Genomic RNA also includes, for example, RNA transcribed from DNA, unprocessed transcripts, mRNAs, and cDNAs. Sometimes the quality and quantity of genomic nucleic acids obtained from samples precludes their usefulness in large scale genotyping studies. To overcome this problem, use of whole genome amplification products and partial genome amplification products allows for characterization of the genome of a sample even if the quantity and quality of the genomic nucleic acid is limited.

Obtaining a Nucleic Acid

Target nucleic acid is obtained from a sample using methods known in the art. Samples include, but are not limited to: biological samples, such as tissue and bodily fluid. For example, samples are obtained from, e.g., blood, urine, serum, lymph, saliva, anal and vaginal secretions, perspiration and semen, skin, organs and the like. Samples are also obtained from the environment (e.g., air, agricultural, water and soil); and research samples (e.g., products of a nucleic acid amplification reaction, or purified genomic DNA, RNA, proteins, etc.).

Isolation, extraction or derivation of genomic nucleic acids is performed by methods known in the art. Isolating nucleic acid from a biological sample generally includes treating a biological sample in such a manner that genomic nucleic acids present in the sample are extracted and made available for analysis. Any isolation method that results in extracted/isolated genomic nucleic may be used in the practice of the present invention.

Nucleic acids may be obtained by methods known in the art. Generally, nucleic acids are extracted using techniques, such as those described in Sambrook, J., Fritsch, E R, and Maniatis, T. (1980)) Molecular Cloning: A Laboratory Manual. 2nd ed. Cold Spring Harbor, N.Y.: Cold Spring Harbor Laboratory.), the contents of which are incorporated by reference herein. Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). Several protocols have been developed to extract genomic DNA from blood.

There are also numerous kits that can be used to extract DNA from tissues and bodily fluids and that are commercially available from, for example, BD Biosciences Clontech (Palo Alto, Calif.), Epicentre Technologies (Madison, Wis.), Gentra Systems, Inc. (Minneapolis, Minn.), MicroProbe Corp. (Bothell, Wash.), Organon Teknika (Durham, N.C.), Qiagen Inc. (Valencia, Calif.), Autogen (Holliston, Mass.); Beckman Coulter (Brea, Calif.), (AutoGenFlex STAR robot with Qiagen FlexiGene chemistry. For example, Autogen manufactures FlexStar automated extraction kits used in combination with Qiagen FlexiGene Chemistry, and Beckeman Coulter manufactures Agencourt GenFind kits for bead-based extraction chemistry. User Guides that describe in detail the protocol(s) to be followed are usually included in all these kits, for example, Qiagen's literature for their PureGene extraction chemistry entitled "Qiagen PureGene Handbook" 3rd Edition, dated June 2011.

After cells have been obtained from the sample, it is preferable to lyse cells in order to isolate genomic nucleic acid. Cellular extracts can be subjected to other steps to drive nucleic acid isolation toward completion by, e.g., differential precipitation, column chromatography, extraction with organic solvents and the like. Extracts then may be further treated, for example, by filtration and/or centrifugation and/or with chaotropic salts such as guanidinium isothiocyanate or urea or with organic solvents such as phenol and/or $HCCl_3$ to denature any contaminating and potentially interfering proteins. The genomic nucleic acid can also be resuspended in a hydrating solution, such as an aqueous buffer. The genomic nucleic acid can be suspended in, for example, water, Tris buffers, or other buffers. In certain embodiments the genomic nucleic acid can be re-suspended in Qiagen DNA hydration solution, or other Tris-based buffer of a pH of around 7.5.

Depending on the type of method used for extraction, the genomic nucleic acid obtained can vary in size. The integrity and size of genomic nucleic acid can be determined by pulse-field gel electrophoresis (PFGE) using an agarose gel.

In addition to genomic nucleic acids, whole genome amplification product and partial genomic amplification products can be used in aspects of the invention. Methods of obtaining whole genome amplification product and partial genome amplification product are described in detail in Pinter et al. U.S. Patent Publication Number 2004/0209299, and include, for example, generally ligation mediated PCR.™, random primed PCR.™, strand displacement mediated PCR.™, and cell immortalization.

Fragmenting the Nucleic Acid

Nucleic acids, including genomic nucleic acids, can be fragmented using any of a variety of methods, such as mechanical fragmenting, chemical fragmenting, and enzymatic fragmenting. Methods of nucleic acid fragmentation are known in the art and include, but are not limited to, DNase digestion, sonication, mechanical shearing, and the like (J. Sambrook et al., "Molecular Cloning: A Laboratory Manual", 1989, 2.sup.nd Ed., Cold Spring Harbour Laboratory Press: New York, N.Y.; P. Tijssen, "Hybridization with Nucleic Acid Probes—Laboratory Techniques in Biochemistry and Molecular Biology (Parts I and II)", 1993, Elsevier; C. P. Ordahl et al., Nucleic Acids Res., 1976, 3: 2985-2999; P. J. Oefner et al., Nucleic Acids Res., 1996, 24:

3879-3889; Y. R. Thorstenson et al., Genome Res., 1998, 8: 848-855). U.S. Patent Publication 2005/0112590 provides a general overview of various methods of fragmenting known in the art.

Genomic nucleic acids can be fragmented into uniform fragments or randomly fragmented. In certain aspects, nucleic acids are fragmented to form fragments having a fragment length of about 5 kilobases or 100 kilobases. In a preferred embodiment, the genomic nucleic acid fragments can range from 1 kilobases to 20 kilobases. Preferred fragments can vary in size and have an average fragment length of about 10 kilobases. However, desired fragment length and ranges of fragment lengths can be adjusted depending on the type of nucleic acid targets one seeks to capture and the design and type of MIP probes. The particular method of fragmenting is selected to achieve the desired fragment length. Numerous non-limiting examples are provided below.

Chemical fragmentation of genomic nucleic acids can be achieved using a number of different methods. For example, hydrolysis reactions including base and acid hydrolysis are common techniques used to fragment nucleic acid. Hydrolysis is facilitated by temperature increases, depending upon the desired extent of hydrolysis. Fragmentation can be accomplished by altering temperature and pH as described below. The benefit of pH-based hydrolysis for shearing is that it can result in single-stranded products. Additionally, temperature can be used with certain buffer systems (e.g. Tris) to temporarily shift the pH up or down from neutral to accomplish the hydrolysis, then back to neutral for long-term storage etc. Both pH and temperature can be modulated to effect differing amounts of shearing (and therefore varying length distributions).

In one aspect, a nucleic acid is fragmented by heating a nucleic acid immersed in a buffer system at a certain temperature for a certain period to time to initiate hydrolysis and thus fragment the nucleic acid. The pH of the buffer system, duration of heating, and temperature can be varied to achieve a desired fragmentation of the nucleic acid. In one embodiment, after a genomic nucleic acid is purified, it is resuspended in a Tris-based buffer at a pH between 7.5 and 8.0, such as Qiagen's DNA hydrating solution. The resuspended genomic nucleic acid is then heated to 65° C. and incubated overnight (about 16-24 hours) at 65° C. Heating shifts the pH of the buffer into the low- to mid-6 range, which leads to acid hydrolysis. Over time, the acid hydrolysis causes the genomic nucleic acid to fragment into single-stranded and/or double-stranded products. The above method of fragmenting can be modified by increasing the temperature and reducing the heating time. For example, a nucleic acid is fragmented by incubating the nucleic acid in the Tris-based buffer at a pH between 7.5 and 8.0 for 15 minutes at 92° C. In addition to adjusting the temperature and the duration of heating, the pH of the Tris-based buffer can be adjusted to achieve a desired nucleic acid fragmentation.

Other methods of hydrolytic fragmenting of nucleic acids include alkaline hydrolysis, formalin fixation, hydrolysis by metal complexes (e.g., porphyrins), and/or hydrolysis by hydroxyl radicals. RNA shears under alkaline conditions, see, e.g. Nordhoff et al., Nucl. Acid. Res., 21 (15):3347-57 (2003), whereas DNA can be sheared in the presence of strong acids or strong bases.

An exemplary acid/base hydrolysis protocol for producing genomic nucleic acid fragments is described in Sargent et al. (1988) Methods Enzymol., 152:432. Briefly, 1 g of purified DNA is dissolved in 50 mL 0.1 N NaOH. 1.5 mL concentrated HCl is added, and the solution is mixed quickly. DNA will precipitate immediately, and should not be stirred for more than a few seconds to prevent formation of a large aggregate. The sample is incubated at room temperature for 20 minutes to partially depurinate the DNA. Subsequently, 2 mL 10 N NaOH ([OH—] concentration to 0.1 N) is added, and the sample is stirred until the DNA redissolves completely. The sample is then incubated at 65° C. for 30 minutes in order to hydrolyze the DNA. Resulting fragments typically range from about 250-1000 nucleotides but can vary lower or higher depending on the conditions of hydrolysis.

Chemical cleavage can also be specific. For example, selected nucleic acid molecules can be cleaved via alkylation, particularly phosphorothioate-modified nucleic acid molecules (see, e.g., K. A. Browne, "Metal ion-catalyzed nucleic Acid alkylation and fragmentation," J. Am. Chem. Soc. 124(27):7950-7962 (2002)). Alkylation at the phosphorothioate modification renders the nucleic acid molecule susceptible to cleavage at the modification site. See I. G. Gut and S. Beck, "A procedure for selective DNA alkylation and detection by mass spectrometry," Nucl. Acids Res. 23(8): 1367-1373 (1995).

Methods of the invention also contemplate chemically shearing nucleic acids using the technique disclosed in Maxam-Gilbert Sequencing Method (Chemical or Cleavage Method), Proc. Natl. Acad. Sci. USA. 74:560-564. In that protocol, the genomic nucleic acid can be chemically cleaved by exposure to chemicals designed to fragment the nucleic acid at specific bases, such as preferential cleaving at guanine, at adenine, at cytosine and thymine, and at cytosine alone.

Mechanical shearing of nucleic acids into fragments can occur using any method known in the art. For example, fragmenting nucleic acids can be accomplished by hydroshearing, trituration through a needle, and sonication. See, for example, Quail, et al. (November 2010) DNA: Mechanical Breakage. In: eLS. John Wiley & Sons, Chichester. doi: 10.1002/9780470015902.a0005 333.pub2.

The nucleic acid can also be sheared via nebulization, see (Roe, B A, Crabtree. J S and Khan, A S 1996); Sambrook & Russell, Cold Spring Harb Protoc 2006. Nebulizing involves collecting fragmented DNA from a mist created by forcing a nucleic acid solution through a small hole in a nebulizer. The size of the fragments obtained by nebulization is determined chiefly by the speed at which the DNA solution passes through the hole, altering the pressure of the gas blowing through the nebulizer, the viscosity of the solution, and the temperature. The resulting DNA fragments are distributed over a narrow range of sizes (700-1330 bp). Shearing of nucleic acids can be accomplished by passing obtained nucleic acids through the narrow capillary or orifice (Oefner et al., Nucleic Acids Res. 1996; Thorstenson et al., Genome Res. 1995). This technique is based on point-sink hydrodynamics that result when a nucleic acid sample is forced through a small hole by a syringe pump.

In HydroShearing (Genomic Solutions, Ann Arbor, Mich., USA), DNA in solution is passed through a tube with an abrupt contraction. As it approaches the contraction, the fluid accelerates to maintain the volumetric flow rate through the smaller area of the contraction. During this acceleration, drag forces stretch the DNA until it snaps. The DNA fragments until the pieces are too short for the shearing forces to break the chemical bonds. The flow rate of the fluid and the size of the contraction determine the final DNA fragment sizes.

Sonication is also used to fragment nucleic acids by subjecting the nucleic acid to brief periods of sonication, i.e. ultrasound energy. A method of shearing nucleic acids into fragments by sonification is described in U.S. Patent Publication 2009/0233814. In the method, a purified nucleic acid is obtained placed in a suspension having particles disposed within. The suspension of the sample and the particles are then sonicated into nucleic acid fragments.

An acoustic-based system that can be used to fragment DNA is described in U.S. Pat. Nos. 6,719,449, and 6,948,843 manufactured by Covaris Inc. U.S. Pat. No. 6,235,501 describes a mechanical focusing acoustic sonication method of producing high molecular weight DNA fragments by application of rapidly oscillating reciprocal mechanical energy in the presence of a liquid medium in a closed container, which may be used to mechanically fragment the DNA.

Another method of shearing nucleic acids into fragments uses ultrasound energy to produce gaseous cavitation in liquids, such as shearing with Diagonnode's BioRuptor®. Cavitation is the formation of small bubbles of dissolved gases or vapors due to the alteration of pressure in liquids. These bubbles are capable of resonance vibration and produce vigorous eddying or microstreaming. The resulting mechanical stress can lead to shearing the nucleic acid in to fragments.

Enzymatic fragmenting, also known as enzymatic cleavage, cuts nucleic acids into fragments using enzymes, such as endonucleases, exonucleases, ribozymes, and DNAzymes. Such enzymes are widely known and are available commercially, see Sambrook, J. Molecular Cloning: A Laboratory Manual, 3rd (2001) and Roberts R J (January 1980). "Restriction and modification enzymes and their recognition sequences," Nucleic Acids Res. 8 (1): r63-r80. Varying enzymatic fragmenting techniques are well-known in the art, and such techniques are frequently used to fragment a nucleic acid for sequencing, for example, Alazard et al, 2002; Bentzley et al, 1998; Bentzley et al, 1996; Faulstich et al, 1997; Glover et al, 1995; Kirpekar et al, 1994; Owens et al, 1998; Pieles et al, 1993; Schuette et al, 1995; Smirnov et al, 1996; Wu & Aboleneen, 2001; Wu et al, 1998a.

The most common enzymes used to fragment nucleic acids are endonucleases. The endonucleases can be specific for either a double-stranded or a single stranded nucleic acid molecule. The cleavage of the nucleic acid molecule can occur randomly within the nucleic acid molecule or can cleave at specific sequences of the nucleic acid molecule. Specific fragmentation of the nucleic acid molecule can be accomplished using one or more enzymes in sequential reactions or contemporaneously.

Restriction endonucleases recognize specific sequences within double-stranded nucleic acids and generally cleave both strands either within or close to the recognition site in order to fragment the nucleic acid. Naturally occurring restriction endonucleases are categorized into four groups (Types I, II III, and IV) based on their composition and enzyme cofactor requirements, the nature of their target sequence, and the position of their DNA cleavage site relative to the target sequence. Bickle T A, Kruger D H (June 1993). "Biology of DNA restriction". Microbiol. Rev. 57 (2): 434-50; Boyer H W (1971). "DNA restriction and modification mechanisms in bacteria". Annu. Rev. Microbiol. 25: 153-76; Yuan R (1981). "Structure and mechanism of multifunctional restriction endonucleases". Annu. Rev. Biochem. 50: 285-319. All types of enzymes recognize specific short DNA sequences and carry out the endonucleolytic cleavage of DNA to give specific fragments with terminal 5'-phosphates. The enzymes differ in their recognition sequence, subunit composition, cleavage position, and cofactor requirements. Williams R J (2003). "Restriction endonucleases: classification, properties, and applications". Mol. Biotechnol. 23 (3): 225-43.

Where restriction endonucleases recognize specific sequencings in double-stranded nucleic acids and generally cleave both strands, nicking endonucleases are capable of cleaving only one of the strands of the nucleic acid into a fragment. Nicking enzymes used to fragment nucleic acids can be naturally occurring or genetically engineered from restriction enzymes. See Chan et al., Nucl. Acids Res. (2011) 39 (1): 1-18.

Denaturing the Nucleic Acid

Methods of the invention also provide for denaturing nucleic acid to render the nucleic acid single stranded for hybridization to a capture probe, such as a MIP probe. Denaturation can result from the fragmentation method chosen, as described above. For example, one skilled in the art recognizes that a genomic nucleic acid can be denatured during pH-based shearing or fragmenting via nicking endonucleases. Denaturation can occur either before, during, or after fragmentation. In addition, the use of pH or heat during the fragmenting step can result in denatured nucleic acid fragments. See, for example, McDonnell, "Antisepsis, disinfection, and sterilization: types, action, and resistance," pg. 239 (2007).

Heat-based denaturing is the process by which double-stranded deoxyribonucleic acid unwinds and separates into single-stranded strands through the breaking of hydrogen bonding between the bases. Heat denaturation of a nucleic acid of an unknown sequence typically uses a temperature high enough to ensure denaturation of even nucleic acids having a very high GC content, e.g., 95° C.-98° C. in the absence of any chemical denaturant. It is well within the abilities of one of ordinary skill in the art to optimize the conditions (e.g., time, temperature, etc.) for denaturation of the nucleic acid. Temperatures significantly lower than 95 C can also be used if the DNA contains nicks (and therefore sticky overhangs of low Tm) or sequence of sufficiently low Tm.

Denaturing nucleic acids with the use of pH is also well known in the art, and such denaturation can be accomplished using any method known in the art such as introducing a nucleic acid to high or low pH, low ionic strength, and/or heat, which disrupts base-pairing causing a double-stranded helix to dissociate into single strands. For methods of pH-based denaturation see, for example, Dore et al. Biophys J. 1969 November; 9(11): 1281-1311; A. M. Michelson The Chemistry of Nucleosides and Nucleotides, Academic Press, London and New York (1963).

Nucleic acids can also be denatured via electro-chemical means, for example, by applying a voltage to a nucleic acid within a solution by means of an electrode. Varying methods of denaturing by applying a voltage are discussed in detail in U.S. Pat. No. 6,197,508 and U.S. Pat. No. 5,993,611.

Molecular Inversion Probe Capture

Molecular inversion probe technology is used to detect or amplify particular nucleic acid sequences in complex mixtures. Use of molecular inversion probes has been demonstrated for detection of single nucleotide polymorphisms (Hardenbol et al. 2005 Genome Res 15:269-75) and for preparative amplification of large sets of exons (Porreca et al. 2007 Nat Methods 4:931-6, Krishnakumar et al. 2008 Proc Natl Acad Sci USA 105:9296-301). One of the main benefits of the method is in its capacity for a high degree of multiplexing, because generally thousands of targets may be captured in a single reaction containing thousands of probes.

In certain embodiments, molecular inversion probes include a universal portion flanked by two unique targeting arms. The targeting arms are designed to hybridize immediately upstream and downstream of a specific target sequence located on a genomic nucleic acid fragment. The molecular inversion probes are introduced to nucleic acid fragments to perform capture of target sequences located on the fragments. According to the invention, fragmenting aids in capture of target nucleic acid by MIP probes. After capture of the target sequence of interest, the captured target may further be subjected to an enzymatic gap-filling and ligation step, such that a copy of the target sequence is incorporated into a circle. Capture efficiency of the MIP to the target sequence on the nucleic acid fragment can be improved by lengthening the hybridization and gap-filing incubation periods. (See, e.g., Turner E H, et al., Nat. Methods. 2009 Apr. 6:1-2.).

The result of MIP capture as described above is a library of circular target probes, which then can be processed in a variety of ways. In one aspect, adaptors for sequencing can be attached during common linker-mediated PCR, resulting in a library with non-random, fixed starting points for sequencing. In another aspect, for preparation of a shotgun library, a common linker-mediated PCR is performed on the circle target probes, and the post-capture amplicons are linearly concatenated, sheared, and attached to adaptors for sequencing. Methods for shearing the linear concatenated captured targets can include any of the methods disclosed for fragmenting nucleic acids discussed above. In certain aspects, performing a hydrolysis reaction on the captured amplicons in the presence of heat is the desired method of shearing for library production.

It should be appreciated that aspects of the invention can involve varying the amounts of genomic nucleic acid and varying the amounts of MIP probes to reach a customized result. In some embodiments, the amount of genomic nucleic acid used per subject ranges from 1 ng to 10 µg (e.g., 500 ng to 5 µg). However, higher or lower amounts (e.g., less than 1 ng, more than 10 µg, 10-50 µg, 50-100 µg or more) may be used. In some embodiments, for each locus of interest, the amount of probe used per assay may be optimized for a particular application. In some embodiments, the ratio (molar ratio, for example measured as a concentration ratio) of probe to genome equivalent (e.g., haploid or diploid genome equivalent, for example for each allele or for both alleles of a nucleic acid target or locus of interest) ranges from 1/100, 1/10, 1/1, 10/1, 100/1, 1000/1. However, lower, higher, or intermediate ratios may be used.

In some embodiments, the amount of target nucleic acid and probe used for each reaction is normalized to avoid any observed differences being caused by differences in concentrations or ratios. In some embodiments, in order to normalize genomic DNA and probe, the genomic DNA concentration is read using a standard spectrophotometer or by fluorescence (e.g., using a fluorescent intercalating dye). The probe concentration may be determined experimentally or using information specified by the probe manufacturer.

Similarly, once a locus has been captured, it may be amplified and/or sequenced in a reaction involving one or more primers. The amount of primer added for each reaction can range from 0.1 pmol to 1 nmol, 0.15 pmol to 1.5 nmol (for example around 1.5 pmol). However, other amounts (e.g., lower, higher, or intermediate amounts) may be used.

In some embodiments, it should be appreciated that one or more intervening sequences (e.g., sequence between the first and second targeting arms on a MIP capture probe), identifier or tag sequences, or other probe sequences that are not designed to hybridize to a target sequence (e.g., a genomic target sequence) should be designed to avoid excessive complementarity (to avoid cross-hybridization) to target sequences or other sequences (e.g., other genomic sequences) that may be in a biological sample. For example, these sequences may be designed to have a sufficient number of mismatches with any genomic sequence (e.g., at least 5, 10, 15, or more mismatches out of 30 bases) or to have a Tm (e.g., a mismatch Tm) that is lower (e.g., at least 5, 10, 15, 20, or more degrees C. lower) than the hybridization reaction temperature.

It should be appreciated that a targeting arm as used herein may be designed to hybridize (e.g., be complementary) to either strand of a genetic locus of interest if the nucleic acid being analyzed is DNA (e.g., genomic DNA). However, in the context of MIP probes, whichever strand is selected for one targeting arm will be used for the other one. However, in the context of RNA analysis, it should be appreciated that a targeting arm should be designed to hybridize to the transcribed RNA. It also should be appreciated that MIP probes referred to herein as "capturing" a target sequence are actually capturing it by template-based synthesis rather than by capturing the actual target molecule (other than for example in the initial stage when the arms hybridize to it or in the sense that the target molecule can remain bound to the extended MIP product until it is denatured or otherwise removed).

It should be appreciated that in some embodiments a targeting arm may include a sequence that is complementary to one allele or mutation (e.g., a SNP or other polymorphism, a mutation, etc.) so that the probe will preferentially hybridize (and capture) target nucleic acids having that allele or mutation. However, in many embodiments, each targeting arm is designed to hybridize (e.g., be complementary) to a sequence that is not polymorphic in the subjects of a population that is being evaluated. This allows target sequences to be captured and/or sequenced for all alleles and then the differences between subjects (e.g., calls of heterozygous or homozygous for one or more loci) can be based on the sequence information and/or the frequency as described herein.

It should be appreciated that sequence tags (also referred to as barcodes) may be designed to be unique in that they do not appear at other positions within a probe or a family of probes and they also do not appear within the sequences being targeted. Thus they can be used to uniquely identify (e.g., by sequencing or hybridization properties) particular probes having other characteristics (e.g., for particular subjects and/or for particular loci).

It also should be appreciated that in some embodiments probes or regions of probes or other nucleic acids are described herein as including certain sequences or sequence characteristics (e.g., length, other properties, etc.). In addition, components (e.g., arms, central regions, tags, primer sites, etc., or any combination thereof) of such probes can include certain sequences or sequence characteristics that consist of one or more characteristics (e.g., length or other properties, ect.).

The invention also contemplates the use of nucleic acid derivatives in the MIPs. As will be described herein, the use of certain nucleic acid derivatives may increase the MIPs of the invention by preventing their digestion, particularly when they are exposed to biological samples that may contain nucleases. As used herein, a nucleic acid derivative is a non-naturally occurring nucleic acid or a unit thereof.

Nucleic acid derivatives may contain non-naturally occurring elements such as non-naturally occurring nucleotides and non-naturally occurring backbone linkages.

Nucleic acid derivatives may contain backbone modifications such as but not limited to phosphorothioate linkages, phosphodiester modified nucleic acids, phosphorothiolate modifications, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The backbone composition of the nucleic acids may be homogeneous or heterogeneous.

Nucleic acid derivatives may contain substitutions or modifications in the sugars and/or bases. For example, they may include nucleic acids having backbone sugars which are covalently attached to low molecular weight organic groups other than a hydroxyl group at the 3' position and other than a phosphate group at the 5' position (e.g., an 2'-0-alkylated ribose group). Nucleic acid derivatives may include non-ribose sugars such as arabinose. Nucleic acid derivatives may contain substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine. In some embodiments, substitution(s) may include one or more substitutions/modifications in the sugars/bases, groups attached to the base, including biotin, fluorescent groups (fluorescein, cyanine, rhodamine, etc), chemically-reactive groups including carboxyl, NHS, thiol, etc., or any combination thereof.

A nucleic acid may be a peptide nucleic acid (PNA), locked nucleic acid (LNA), DNA, RNA, or co-nucleic acids of the same such as DNA-LNA co-nucleic acids. PNA are DNA analogs having their phosphate backbone replaced with 2-aminoethyl glycine residues linked to nucleotide bases through glycine amino nitrogen and methylenecarbonyl linkers. PNA can bind to both DNA and RNA targets by Watson-Crick base pairing, and in so doing form stronger hybrids than would be possible with DNA or RNA based oligonucleotides in some cases.

PNA are synthesized from monomers connected by a peptide bond (Nielsen, P. E. et al. Peptide Nucleic Acids, Protocols and Applications, Norfolk: Horizon Scientific Press, p. 1-19 (1999)). They can be built with standard solid phase peptide synthesis technology. PNA chemistry and synthesis allows for inclusion of amino acids and polypeptide sequences in the PNA design. For example, lysine residues can be used to introduce positive charges in the PNA backbone. All chemical approaches available for the modifications of amino acid side chains are directly applicable to PNA. Several types of PNA designs exist, and these include single strand PNA (ssPNA), bisPNA and pseudo-complementary PNA (pcPNA).

The structure of PNA/DNA complex depends on the particular PNA and its sequence. ssPNA binds to single stranded DNA (ssDNA) preferably in antiparallel orientation (i.e., with the N-terminus of the ssPNA aligned with the 3' terminus of the ssDNA) and with a Watson-Crick pairing. PNA also can bind to DNA with a Hoogsteen base pairing, and thereby forms triplexes with double stranded DNA (dsDNA) (Wittung, P. et al., Biochemistry 36:7973 (1997)).

A locked nucleic acid (LNA) is a modified RNA nucleotide. An LNA form hybrids with DNA, which are at least as stable as PNA/DNA hybrids (Braasch, D. A. et al., Chem & Biol. 8(1):1-7 (2001)). Therefore, LNA can be used just as PNA molecules would be. LNA binding efficiency can be increased in some embodiments by adding positive charges to it. LNAs have been reported to have increased binding affinity inherently.

Commercial nucleic acid synthesizers and standard phosphoramidite chemistry are used to make LNAs. Therefore, production of mixed LNA/DNA sequences is as simple as that of mixed PNA/peptide sequences. The stabilization effect of LNA monomers is not an additive effect. The monomer influences conformation of sugar rings of neighboring deoxynucleotides shifting them to more stable configurations (Nielsen, P. E. et al. Peptide Nucleic Acids, Protocols and Applications, Norfolk: Horizon Scientific Press, p. 1-19 (1999)). Also, lesser number of LNA residues in the sequence dramatically improves accuracy of the synthesis. Most of biochemical approaches for nucleic acid conjugations are applicable to LNA/DNA constructs.

While probes have been typically designed to meet certain constraints (e.g. melting temperature, G/C content, etc.) known to partially affect capture/amplification efficiency (Ball et al (2009) Nat Biotech 27:361-8 AND Deng et al (2009) Nat Biotech 27:353-60), a set of constraints which is sufficient to ensure either largely uniform or highly reproducible capture/amplification efficiency has not previously been achieved.

As disclosed herein, uniformity and reproducibility can be increased by designing multiple probes per target, such that each base in the target is captured by more than one probe. In some embodiments, the disclosure provides multiple MIPs per target to be captured, where each MIP in a set designed for a given target nucleic acid has a central region and a 5' region and 3' region ('targeting arms') which hybridize to (at least partially) different nucleic acids in the target nucleic acid (immediately flanking a subregion of the target nucleic acid). Thus, differences in efficiency between different targeting arms and fill-in sequences may be averaged across multiple MIPs for a single target, which results in more uniform and reproducible capture efficiency.

In some embodiments, the methods involve designing a single probe for each target (a target can be as small as a single base or as large as a kilobase or more of contiguous sequence).

It may be preferable, in some cases, to design probes to capture molecules (e.g., target nucleic acids or subregions thereof) having lengths in the range of 1-200 bp (as used herein, a by refers to a base pair on a double-stranded nucleic acid—however, where lengths are indicated in bps, it should be appreciated that single-stranded nucleic acids having the same number of bases, as opposed to base pairs, in length also are contemplated by the invention). However, probe design is not so limited. For example, probes can be designed to capture targets having lengths in the range of up to 10, 20, 30, 40, 50, 60, 70, 80, 90, 100, 200, 300, 400, 500, 1000, or more bps, in some cases.

It is to be appreciated that the length of a capture molecule on a nucleic acid fragment (e.g., a target nucleic acid or subregion thereof) is selected based upon multiple considerations. For example, where analysis of a target involves sequencing, e.g., with a next-generation sequencer, the target length should typically match the sequencing read-length so that shotgun library construction is not necessary. However, it should be appreciated that captured nucleic acids may be sequenced using any suitable sequencing technique as aspects of the invention are not limited in this respect.

It is also to be appreciated that some target nucleic acids on a nucleic acid fragment are too large to be captured with one probe. Consequently, it may be necessary to capture multiple subregions of a target nucleic acid in order to analyze the full target.

In some embodiments, a sub-region of a target nucleic acid is at least 1 bp. In other embodiments, a subregion of a target nucleic acid is at least 10, 20, 30, 40, 50, 60, 70, 80, 90, 100, 200, 300, 400, 500, 600, 700, 800, 900, 1000 bp or more. In other embodiments, a subregion of a target nucleic acid has a length that is up to 10%, 20%, 30%, 40%, 50%, 60%, 70%, 80%, 90%, 95%, or more percent of a target nucleic acid length.

The skilled artisan will also appreciate that consideration is made, in the design of MIPs, for the relationship between probe length and target length. In some embodiments, MIPs are designed such that they are several hundred basepairs (e.g., up to 100, 200, 300, 400, 500, 600, 700, 800, 900, 1000 bp or more) longer than corresponding target (e.g., subregion of a target nucleic acid, target nucleic acid). In some embodiments, lengths of subregions of a target nucleic acid may differ.

For example, if a target nucleic acid contains regions for which probe hybridization is not possible or inefficient, it may be necessary to use probes that capture subregions of one or more different lengths in order to avoid hybridization with problematic nucleic acids and capture nucleic acids that encompass a complete target nucleic acid.

Methods of the invention also provide for combining the method of fragmenting the nucleic acid prior to capture with other MIP capture techniques that are designed to increase target uniformity, reproducibility, and specificity. Other MIP capture techniques are shown in co-owned and pending application, U.S. patent application Ser. No. 13/266,862, "Methods and Compositions for Evaluating Genetic Markers."

For example, multiple probes, e.g., MIPs, can be used to amplify each target nucleic acid. In some embodiments, the set of probes for a given target can be designed to 'tile' across the target, capturing the target as a series of shorter sub targets. In some embodiments, where a set of probes for a given target is designed to 'tile' across the target, some probes in the set capture flanking non-target sequence). Alternately, the set can be designed to 'stagger' the exact positions of the hybridization regions flanking the target, capturing the full target (and in some cases capturing flanking non-target sequence) with multiple probes having different targeting arms, obviating the need for tiling. The particular approach chosen will depend on the nature of the target set. For example, if small regions are to be captured, a staggered-end approach might be appropriate, whereas if longer regions are desired, tiling might be chosen. In all cases, the amount of bias-tolerance for probes targeting pathological loci can be adjusted by changing the number of different MIPs used to capture a given molecule.

In some embodiments, the 'coverage factor', or number of probes used to capture a basepair in a molecule, is an important parameter to specify. Different numbers of probes per target are indicated depending on whether one is using the tiling approach (see, e.g., FIG. 1) or one of the staggered approaches (see, e.g., FIG. 2 or 3).

FIG. 1 illustrates a non-limiting embodiment of a tiled probe layout showing ten captured sub-targets tiled across a single target. Each position in the target is covered by three sub-targets such that MIP performance per base pair is averaged across three probes.

Figure 2:
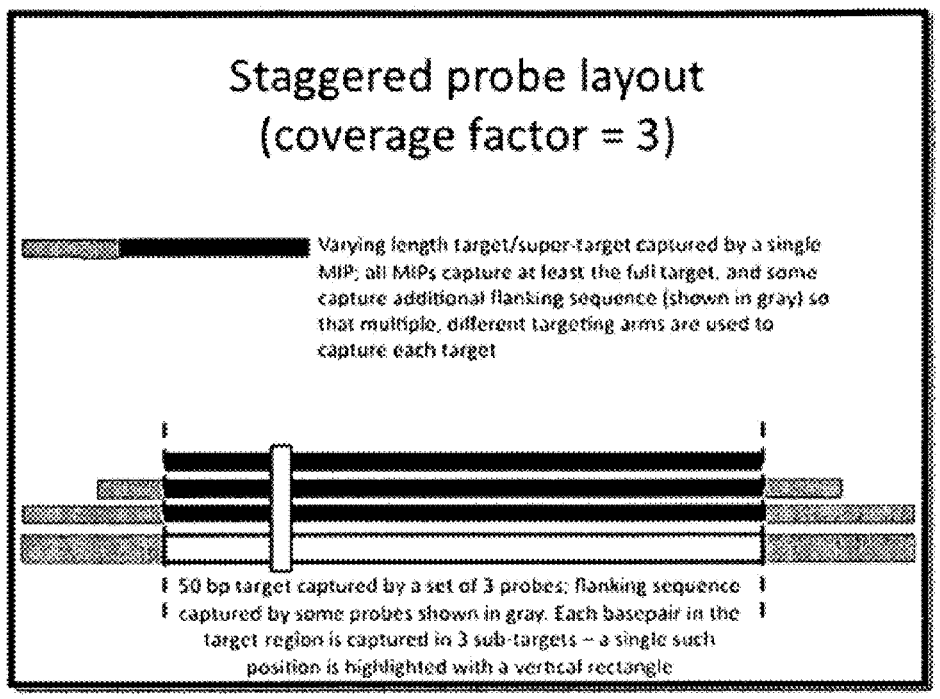
FIG. 2 illustrates a non-limiting embodiment of a staggered probe layout.

FIG. 2 illustrates a non-limiting embodiment of a staggered probe layout showing the targets captured by a set of three MIPs. Each MIP captures the full target, shown in black, plus (in some cases) additional extra-target sequence, shown in gray, such that the targeting arms of each MIP fall on different sequence. Each position in the target is covered by three sub-targets such that MIP performance per basepair is averaged across three probes. Targeting arms land immediately adjacent to the black or gray regions shown. It should be appreciated that in some embodiments, the targeting arms (not shown) can be designed so that they do not overlap with each other.

Figure 3:
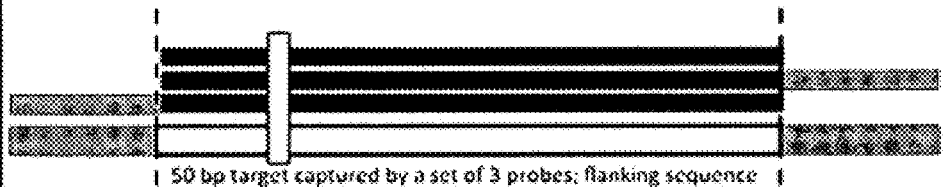
FIG. 3 illustrates a non-limiting embodiment of an alternating staggered probe layout.

FIG. 3 illustrates a non-limiting embodiment of an alternating staggered probe layout showing the targets captured by a set of three MIPs. Each MIP captures the full target, shown in black, plus (in some cases) additional extra-target sequence, shown in gray, such that the targeting arms of each MIP fall on different sequence. Each position in the target is covered by three sub-targets such that MIP performance per basepair is averaged across three probes. Targeting arms land immediately adjacent to the black or gray regions shown.

It should be appreciated that for any of the layouts, the targeting arms on adjacent tiled or staggered probes may be designed to either overlap, not overlap, or overlap for only a subset of the probes.

In certain embodiments for any of the layouts, a coverage factor of about 3 to about 10 is used. However, the methods are not so limited and coverage factors of up to 2, 3, 4, 5, 6, 7, 8, 9, 10, 20 or more may be used. It is to be appreciated that the coverage factor selected may depend the probe layout being employed. For example, in the tiling approach, for a desired coverage factor, the number of probes per target is typically a function of target length, sub-target length, and spacing between adjacent sub-target start locations (step size). For example, for a desired coverage factor of 3, a 200 bp target with a start-site separation of 20 bp and sub-target length of 60 bp may be encompassed with 12 MIPs (FIG. 1). Thus, a specific coverage factor may be achieved by varying the number of probes per target nucleic acid and the length of the molecules captured. In the staggered approach, a fixed-length target nucleic acid is captured as several sub-regions or as 'super-targets', which are molecules comprising the target nucleic acid and additional flanking nucleic acids, which may be of varying lengths. For example, a target of 50 bp can be captured at a coverage factor of 3 with 3 probes in either a 'staggered' (FIG. 2) or 'alternating staggered' configuration (FIG. 3).

The coverage factor will be driven by the extent to which detection bias is tolerable. In some cases, where the bias tolerance is small, it may be desirable to target more subregions of target nucleic acid with, perhaps, higher coverage factors. In some embodiments, the coverage factor is up to 2, 3, 4, 5, 6, 7, 8, 9, 10 or more.

In some embodiments, when a tiled probe layout is used, when the target length is greater than 1 bp and when a step size (distance between the 5'-end of a target and the 5' end of its adjacent target) is less than the length of a target or subregion thereof, it is possible to compute probe number for a particular target based on target length (T), sub target length (S), and coverage factor (C), such that probe number=T/(S/C)+(C−1).

In some aspects, the disclosure provides methods to increase the uniformity of amplification efficiency when multiple molecules are amplified in parallel; methods to increase the reproducibility of amplification efficiency; methods to reduce the contribution of targeting probe variability to amplification efficiency; methods to reduce the effect on a given target nucleic acid of polymorphisms in probe hybridization regions; and/or methods to simplify downstream workflows when multiplex amplification by MIPs is used as a preparative step for analysis by nucleic acid sequencing.

Polymorphisms in the target nucleic acid under the regions flanking a target can interfere with hybridization, polymerase fill-in, and/or ligation. Furthermore, this may occur for only one allele, resulting in allelic drop-out, which ultimately decreases downstream sequencing accuracy. In some embodiments, using a set of MIPs having multiple hybridization sites for the capture of any given target, the probability of loss from polymorphism is substantially decreased because not all targeting arms in the set of MIPs will cover the location of the mutation.

Probes for MIP capture reactions may be synthesized on programmable microarrays because of the large number of sequences required. Because of the low synthesis yields of these methods, a subsequent amplification step is required to produce sufficient probe for the MIP amplification reaction. The combination of multiplex oligonucleotide synthesis and pooled amplification results in uneven synthesis error rates and representational biases. By synthesizing multiple probes for each target, variation from these sources may be averaged out because not all probes for a given target will have the same error rates and biases.

Applications

Multiplex amplification strategies disclosed herein may be used analytically, as in detection of SNPs, or preparatively, often for next-generation sequencing or other sequencing techniques. In the preparative setting, the output of an amplification reaction is generally the input to a shotgun library protocol, which then becomes the input to the sequencing platform. The shotgun library is necessary in part because next-generation sequencing yields reads significantly shorter than amplicons such as exons. In addition to the bias-reduction afforded by the multi-tiled approach described here, tiling also obviates the need for shotgun library preparation. Since the length of the capture molecule can be specified when the probes, e.g., MIPs, are designed, it can be chosen to match the readlength of the sequencer. In this way, reads can 'walk' across an exon by virtue of the start position of each capture molecule in the probe set for that exon. Reducing analytical errors associated with bias in nucleic acid preparations:

In some embodiments, aspects of the invention relate to preparative steps in DNA sequencing-related technologies that reduce bias and increase the reliability and accuracy of downstream quantitative applications.

There are currently many genomics assays that utilize next-generation (polony-based) sequencing to generate data, including genome resequencing, RNA-seq for gene expression, bisulphite sequencing for methylation, and Immuneseq, among others. In order to make quantitative measurements (including genotype calling), these methods utilize the counts of sequencing reads of a given genomic locus as a proxy for the representation of that sequence in the original sample of nucleic acids. The majority of these techniques require a preparative step to construct a high-complexity library of DNA molecules that is representative of a sample of interest. This may include chemical or biochemical treatment of the DNA (e.g., bisulphite treatment), capture of a specific subset of the genome (e.g., padlock probe capture, solution hybridization), and a variety of amplification techniques (e.g., polymerase chain reaction, whole genome amplification, rolling circle amplification).

Systematic and random errors are common problems associated with genome amplification and sequencing library construction techniques. For example, genomic sequencing library may contain an over- or under-representation of particular sequences from a source genome as a result of errors (bias) in the library construction process. Such bias can be particularly problematic when it results in target sequences from a genome being absent or undetectable in the sequencing libraries. For example, an under representation of particular allelic sequences (e.g., heterozygotic alleles) from a genome in a sequencing library can result in an apparent homozygous representation in a sequencing library. As most downstream sequencing library quantification techniques depend on stochastic counting processes, these problems have typically been addressed by sampling enough (over-sampling) to obtain a minimum number of observations necessary to make statistically significant decisions. However, the strategy of oversampling is generally limited to elimination of low-count Poisson noise, and the approach wastes resources and increases the expense required to perform such experiments. Moreover, oversampling can result in a reduced statistical confidence in certain conclusions (e.g., diagnostic calls) based on the data. Accordingly, new approaches are needed for overcoming bias in sequencing library preparatory methods.

Aspects of the disclosure are based, in part, on the discovery of methods for overcoming problems associated with systematic and random errors (bias) in genome capture, amplification and sequencing methods, namely high variability in the capture and amplification of nucleic acids and disproportionate representation of heterozygous alleles in sequencing libraries. Accordingly, in some embodiments, the disclosure provides methods that reduce variability in the capture and amplification of nucleic acids. In other embodiments, the methods improve allelic representation in sequencing libraries and, thus, improve variant detection outcomes. In certain embodiments, the disclosure provides preparative methods for capturing target nucleic acids (e.g., genetic loci) that involve the use of differentiator tag sequences to uniquely tag individual nucleic acid molecules. In some embodiments, the differentiator tag sequence permits the detection of bias based on the frequency with which pairs of differentiator tag and target sequences are observed in a sequencing reaction. In other embodiments, the methods reduce errors caused by bias, or the risk of bias, associated with the capture, amplification and sequencing of genetic loci, e.g., for diagnostic purposes.

Aspects of the invention relate to associating unique sequence tags (referred to as differentiator tag sequences) with individual target molecules that are independently captured and/or analyzed (e.g., prior to amplification or other process that may introduce bias). These tags are useful to distinguish independent target molecules from each other thereby allowing an analysis to be based on a known number of individual target molecules. For example, if each of a plurality of target molecule sequences obtained in an assay is associated with a different differentiator tag, then the target sequences can be considered to be independent of each other and a genotype likelihood can be determined based on this information. In contrast, if each of the plurality of target molecule sequences obtained in the assay is associated with the same differentiator tag, then they probably all originated from the same target molecule due to over-representation (e.g., due to biased amplification) of this target molecule in the assay. This provides less information than the situation where each nucleic acid was associated with a different differentiator tag. In some embodiments, a threshold number of independently isolated molecules (e.g., unique combinations of differentiator tag and target sequences) is analyzed to determine the genotype of a subject.

In some embodiments, the invention relates to compositions comprising pools (libraries) of preparative nucleic acids that each comprise "differentiator tag sequences" for detecting and reducing the effects of bias, and for genotyping target nucleic acid sequences. As used herein, a "differentiator tag sequence" is a sequence of a nucleic acid (a preparative nucleic acid), which in the context of a plurality of different isolated nucleic acids, identifies a unique, independently isolated nucleic acid. Typically, differentiator tag sequences are used to identify the origin of a target nucleic acid at one or more stages of a nucleic acid preparative method. For example, in the context of a multiplex nucleic acid capture reaction, differentiator tag sequences provide a basis for differentiating between multiple independent, target nucleic acid capture events. Also, in the context of a multiplex nucleic acid amplification reaction, differentiator tag sequences provide a basis for differentiating between multiple independent, primary amplicons of a target nucleic acid, for example. Thus, combinations of target nucleic acid and differentiator tag sequence (target:differentiator tag sequences) of an isolated nucleic acid of a preparative method provide a basis for identifying unique, independently isolated target nucleic acids.

It will be apparent to the skilled artisan that differentiator tags may be synthesized using any one of a number of different methods known in the art. For example, differentiator tags may be synthesized by random nucleotide addition.

Differentiator tag sequences are typically of a predefined length, which is selected to control the likelihood of producing unique target:differentiator tag sequences in a preparative reaction (e.g., amplification-based reaction, a circularization selection-based reaction, e.g., a MIP reaction). Differentiator tag sequences may be, up to 5, up to 6, up to 7 up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, or more nucleotides in length. For purposes of genotyping, isolated nucleic acids are identified as independently isolated if they comprise unique combinations of target nucleic acid and differentiator tag sequences, and observance of threshold numbers of unique combinations of target nucleic acid and differentiator tag sequences provide a certain statistical confidence in the genotype.

During a library preparation process, each nucleic acid molecule may be tagged with a unique differentiator tag sequence in a configuration that permits the differentiator tag sequence to be sequenced along with the target nucleic acid sequence of interest (the nucleic acid sequence for which the library is being prepared, e.g., a polymorphic sequence). The incorporation of the nucleic acid comprising a differentiator tag sequence at a particular step allows the detection and correction of biases in subsequent steps of the protocol.

A large library of unique differentiator tag sequences may be created by using degenerate, random-sequence polynucleotides of defined length. The differentiator tag sequences of the polynucleotides may be read at the final stage of the sequencing. The observations of the differentiator tag sequences may be used to detect and correct biases in the final sequencing read-out of the library. For example, the total possible number of differentiator tag sequences, which may be produced, e.g., randomly, is $4^N$, where N is the length of the differentiator tag sequence. Thus, it is to be understood that the length of the differentiator tag sequence may be adjusted such that the size of the population of MIPs having unique differentiator tag sequences is sufficient to produce a library of MIP capture products in which identical independent combinations of target nucleic acid and differentiator tag sequence are rare. As used herein combinations of target nucleic acid and differentiator tag sequences, may also be referred to as "target:differentiator tag sequences".

In the final readout of a sequencing process, each read may have an additional unique differentiator tag sequence. In some embodiments, when differentiator tag sequences are distributed randomly in a library, all the unique differentiator tag sequences will be observed about an equal number of times. Accordingly, the number of occurrences of a differentiator tag sequence may follow a Poisson distribution.

In some embodiments, overrepresentation of target:differentiator tag sequences in a pool of preparative nucleic acids (e.g., amplified MIP capture products) is indicative of bias in the preparative process (e.g., bias in the amplification process). For example, target:differentiator tag sequence combinations that are statistically overrepresented are indicative of bias in the protocol at one or more steps between the incorporation of the differentiator tag sequences into MIPs and the actual sequencing of the MIP capture products.

The number of reads of a given target:differentiator tag sequence may be indicative (may serve as a proxy) of the amount of that target sequence present in the originating sample. In some embodiments, the numbers of occurrence of sequences in the originating sample is the quantity of interest. For example, using the methods disclosed herein, the occurrence of differentiator tag sequences in a pool of MIPs may be predetermined (e.g., may be the same for all differentiator tag sequences). Accordingly, changes in the occurrence of differentiator tag sequences after amplification and sequencing may be indicative of bias in the protocol. Bias may be corrected to provide an accurate representation of the composition of the original MIP pool, e.g., for diagnostic purposes.

According to some aspects, a library of preparative nucleic acid molecules (e.g., MIPs, each nucleic acid in the library having a unique differentiator tag sequence, may be constructed such that the number of nucleic acid molecules in the library is significantly larger than the number prospective target nucleic acid molecules to be captured using the library. This ensures that products of the preparative methods include only unique target:differentiator tag sequence; e.g., in a MIP reaction the capture step would under sample the total population of unique differentiator tag sequences in the MIP library. For example, an experiment utilizing 1 ug of genomic DNA will contain about ~150,000 copies of a diploid genome. For a MIP library, each MIP in the library comprising a randomly produced 12-mer differentiator tag sequence (~1.6 million possible unique differentiator tag sequences), there would be more than 100 unique differentiator tag sequences per genomic copy. For a MIP library, each MIP in the library comprising a randomly produced 15-mer differentiator tag sequence (~1 billion possible unique differentiator tag sequences), there would be more than 7000 unique differentiator tag sequences per genomic copy. Therefore, the probability of the same differentiator tag sequence being incorporated multiple times is incredibly small. Thus, it is to be appreciated that the length of the differentiator tag sequence is to be selected based on the amount of target sequence in a MIP capture reaction and the desired probability for having multiple, independent occurrences of target:differentiator tag sequence combinations.

The skilled artisan will appreciate that as part of a MIP library preparation process, adapters may be ligated onto the ends of the molecules of interest. Adapters often contain PCR primer sites (for amplification or emulsion PCR) and/or sequencing primer sites. In addition, barcodes may be included, for example, to uniquely identify individual samples (e.g., patient samples) that may be mixed together. (See, e.g., USPTO Publication Number US 2007/0020640 A1 (McCloskey et al.)

The actual incorporation of the random differentiator tag sequences can be performed through various methods known in the art. For example, nucleic acids comprising differentiator tag sequences may be incorporated by ligation. This is a flexible method, because molecules having differentiator tag sequence can be ligated to any blunt-ended nucleic acids. The sequencing primers must be incorporated subsequently such that they sequence both the differentiator tag sequence and the target sequence. Alternatively, the sequencing adaptors can be synthesized with the random differentiator tag sequences at their 3' end (as degenerate bases), so that only one ligation must be performed. Another method is to incorporate the differentiator tag sequence into a PCR primer, such that the primer structure is arranged with the common adaptor sequence followed by the random differentiator tag sequence followed by the PCR priming sequence (in 5' to 3' order). A differentiator tag sequence and adaptor sequence (which may contain the sequencing primer site) are incorporated as tags. Another method to incorporate the differentiator tag sequences is to synthesize them into a padlock probe prior to performing a gene capture reaction. The differentiator tag sequence is incorporated 3' to the targeting arm but 5' to the amplification primer that will be used downstream in the protocol. Another method to incorporate the differentiator tag sequences is as a tag on a gene-specific or poly-dT reverse-transcription primer. This allows the differentiator tag sequence to be incorporated directly at the cDNA level.

In some embodiments, at the incorporation step, the distribution of differentiator tag sequences can be assumed to be uniform. In this case, bias in any part of the protocol would change the uniformity of this distribution, which can be observed after sequencing. This allows the differentiator tag sequence to be used in any preparative process where the ultimate output is sequencing of many molecules in parallel.

Differentiator tag sequences may be incorporated into probes (e.g., MIPs) of a plurality when they are synthesized on-chip in parallel, such that degeneracy of the incorporated nucleotides is sufficient to ensure near-uniform distribution in the plurality of probes. It is to be appreciated that amplification of a pool of unique differentiator tag sequences may itself introduce bias in the initial pool. However, in most practical cases, the scale of synthesis (e.g., by column synthesis, chip based synthesis, etc.) is large enough that amplification of an initial pool of differentiator tag sequences is not necessary. By avoiding amplification or selection steps on the pool of unique differentiator tag sequences, potential bias may be minimized.

One example of the use of the differentiator tag sequences is in genome re-sequencing. Considering that the raw accuracy of most next-generation sequencing instruments is relatively low, it is crucial to oversample the genomic loci of interest.

Furthermore, since there are two alleles at every locus, it is important to sample enough to ensure that both alleles have been observed a sufficient number of times to determine with a sufficient degree of statistical confidence whether the sample is homozygous or heterozygous. Indeed, the sequencing is performed to sample the composition of molecules in the originating sample. However, after multiple reads have been collected for a given locus, it is possible that due to bias (e.g., caused by PCR amplification steps), a large fraction of the reads are derived from a single originating molecule. This would skew the population of target sequences observed, and would affect the outcome of the genotype call. For example, it is possible that a locus that is heterozygous is called as homozygous, because there are only a few observations of the second allele out of many observations of that locus. However, if information is available on differentiator tag sequences, this situation could be averted, because the over-represented allele would be seen to also have an over-represented differentiator tag sequence (i.e., the sequences with the overrepresented differentiator tag sequence all originated from the same single molecule). Therefore, the sequences and corresponding distribution of differentiator tag sequences can be used as an additional input to the genotype-calling algorithm to significantly improve the accuracy and confidence of the genotype calls.

EXAMPLE

Molecular Inversion Probe Capture on Fragmented Genomic DNA

The following example shows a preferred method of practicing the invention.

Genomic DNA was extracted from whole human blood using a Gentra Puregene Blood Kit and following the Puregene protocol for DNA Purification from Whole Blood (Qiagen). The protocol can be scaled (i.e. amount of solution, duration) to accommodate the desired amount of whole genomic DNA.

First, a red blood cell Lysis Solution was dispensed into a centrifuge tube, and 2.0 ml of human whole blood was added. The sample was mixed by inverting 10 times. Then, the sample was incubated at room temperature and inverted at least once during the incubation for approximately 5 minutes. After incubation, the sample was centrifuged for a time period sufficient to pellet the white blood cells. Once white blood cells pelleted, supernatant was discarded by pipetting or pouring while leaving the residual liquid and white blood cell pellet in the tube. The remaining residual liquid and white blood cell pellet was vortexed vigorously to resuspend the pellet in residual liquid. Cell lysis solution was then added, and vortexed vigously for 10 seconds. RNase A solution was added and mixed in by inverting the tube 25 times. The sample was incubated at 37° C. for 30 minutes, vortexing briefly every 15 minutes. Protein precipitation solution was then added and the sample was vortexed. The sample was then centrifuged so that the precipitated proteins formed a tight brown pellet. Supernatant was poured into another centrifuge tube containing isopropanol. The tube was inverted gently until DNA was visible as threads or a clump. After which, the sample was centrifuged. The resulting supernatant was then discarded, and the residual liquid was removed by pipetting, but leaving the pellet within in the tube. A 70% ethanol solution was added to the tube to wash the DNA pellet. The tube was then centrifuged, after which the supernatant was discarded by draining the tube, taking care that the DNA pellet remained. A DNA hydration solution, a Tris-based buffer at a pH between 7.5 and 8.0, was then added to the sample, and the sample was then vortexed to mix. This provided a sample of isolated whole genomic DNA in DNA hydrating solution.

In order to fragment and denature the genomic DNA, the isolated whole genomic DNA was incubated in the DNA hydrating solution, i.e. the Tris-based buffer at a pH between 7.5 and 8.0, for 16-24 hours at 65° C.

Once isolated, MIP capture probes were hybridized to the isolated fragmented genomic DNA by introducing the fragmented genomic DNA to 1.0 ul capture probe mix (~2.5 pmol), 2.0 ul 10× Ampligase buffer (Epicentre), and 11 ul dH$_2$O. The reaction was incubated at 60° C. for 40 hours. The capture probe mix used for the capture reaction contained MIP probes having targeting arm sequences that were different for each capture probe in a set, while constant region sequence will be the same for all probes in the set, allowing all captured targets to be amplified with a single set of primers. Targeting arm sequences were designed such that any given pair of 20 bp sequences is unique in the target genome (to prevent spurious capture of undesired sites). Additionally, melting temperatures were matched for all probes in the set such that hybridization efficiency was uniform for all probes at a constant temperature (e.g., 60° C.). The reaction was incubated at various temperatures to promote hybridization.

The hybridized probes were converted into covalently-closed circular products containing subtargets by preparing a filling-in/ligation reaction mixture, adding the mixture to the hybridized probe reaction, and incubating the reaction at 60° C. for 10 hours. The Prepared fill-in/ligation reaction mixture included 1.0 ul, 2 mM dNTP mix (Invitrogen), 2.0 ul, 10× Ampligase buffer (Epicentre), 5 U/ul Taq Stoffel fragment (Applied Biosystems), 5 U/ul Ampligase (Epicentre), and 4.75 ul dH20.

The circularized probe/subtarget products were then purified from un-reacted probes and genomic DNA. An exonuclease reaction mixture was prepared by mixing 21 ul of the fill-in/ligation reaction product with 2.0 ul 10× exonuclease I buffer (New England Biolabs), 2.0 ul 20 U/ul exonuclease I (New England Biolabs), 2.0 ul 100 U/ul exonuclease III (New England Biolabs). The reaction was incubated at 37° C. for 60 min, then heat-inactivate by incubating at 80° C. for 15 min, thus producing a heat-inactivated exonuclease reaction mixture. The heat inactivated exonuclease reaction mixture was then immediately cooled to 4° C. for storage.

Next, the purified circular material was amplified using PCR primers specific to the 'constant region' of the probes. To perform the amplification, a PCR mixture was prepared by mixing the 2.0 ul of the heat-inactivated exonuclease reaction mixture with 5.0 ul 10× Accuprime reaction buffer (Invitrogen), 1.5 ul 10 uM CP-2-FA (5'-GCACGATC-CGACGGTAGTGT-3') (SEQ ID NO: 1), 1.5 ul 10 uM CP-2-RA (5'-CCGTAATCGGGAAGCTGAAG-3') (SEQ ID NO: 2), 0.4 ul 25 mM dNTP mix (Invitrogen), 1.5 ul 10× SybrGreen (Invitrogen), 0.4 ul 2.5 U/ul Accuprime Pfx polymerase (Invitrogen) and 37.7 ul dH20.

The PCR mixture was thermal cycled in real-time thermal cycler according to the following protocol, but cycling was stopped before amplification yield plateaus (generally 8-12 cycles): 1) 95° C. for 5 min; 2) 95° C. for 30 sec; 3) 58° C. for 60 sec; 4) 72° C. for 60 sec; and 5) two cycles of 95° C. for 30 sec.

After PCR, a shotgun next-generation sequencing library was prepared by the following steps. The desired amplicon population was purified from non-specific amplification products by gel extraction. The amplicons were concatemerized into high-molecular weight products suitable for fragmentation. The concatemerized amplicons incubated in a Tris-buffer at a pH between 7.5 and 8.0 for 16 hrs at 65° C. in order to fragment the amplicons. Adapters required for amplification by the sequencing platform were then ligated to the fragmented amplicons.

INCORPORATION BY REFERENCE

References and citations to other documents, such as patents, patent applications, patent publications, journals, books, papers, web contents, have been made throughout this disclosure. All such documents are hereby incorporated herein by reference in their entirety for an purposes.

EQUIVALENTS

The invention may be embodied in other specific forms without departing from the spirit or essential characteristics thereof. The foregoing embodiments are therefore to be considered in an respects illustrative rather than limiting on the invention described herein.

What is claimed is:

1. A method of performing a molecular inversion probe capture reaction, the method comprising:
  denaturing a nucleic acid;
  fragmenting the nucleic acid into nucleic acid fragments in order to expose a target site for a molecular inversion probe that was not exposed prior to fragmenting, wherein the fragmenting step occurs during the denaturing step, and wherein the nucleic acid is fragmented and denatured by heating the nucleic acid in a buffer system to shift a pH of the buffer system;
  introducing a plurality of molecular inversion probes under conditions such that the molecular inversion probe hybridizes to the target site on the nucleic acid fragment, and wherein each of the plurality of molecular inversion probes is configured to capture a different subregion of the target site, and wherein each subregion is different and overlaps with at least one other subregion on the same strand;
  circularizing the hybridized molecular inversion probe to form a circularized probe/target nucleic acid molecule;
  isolating the circularized probe/target nucleic acid molecule;
  linearizing the circularized probe/target nucleic acid molecule, thereby forming a linearized probe/target nucleic acid molecule;
  conducting an amplification reaction with the linearized probe/target nucleic acid molecule to generate an amplification product, wherein the amplification reaction introduces a barcode sequence to the amplification product; and
  sequencing the amplification product.

2. The method of claim 1, further comprising the step of denaturing the nucleic acid or at least one nucleic acid fragment prior to the capturing step.

3. The method of claim 1, wherein the nucleic acid fragments are from about 5 kb to about 100 kb in length.

4. The method of claim 1, wherein the nucleic acid fragments are from about 1 kb to about 10 kb in length.

5. The method of claim 1, wherein the nucleic acid is selected from the group of genomic DNA, genomic RNA, whole or partial genome amplification product, high molecular weight DNA, and high molecular weight RNA.

6. A method of improving performance of capture reactions using molecular inversion probes having two targeting arms, the method comprising:
  denaturing a nucleic acid;
  fragmenting the nucleic acid into nucleic acid fragments in order to expose a target site having one or more bases to molecular inversion probes that were not exposed prior to fragmenting, the molecular inversion probes being designed such that each molecular inversion probes is configured to capture a different subregion of the target site, and wherein each subregion is different and overlaps with at least one other subregion on the same strand, wherein the fragmenting step occurs during the denaturing step, and wherein the nucleic acid is fragmented and denatured by heating the nucleic acid in a buffer system to shift a pH of the buffer system;
  introducing the molecular inversion probes under conditions such that the molecular inversion probes hybridize to the target site on the nucleic acid fragment;
  circularizing the hybridized molecular inversion probes to form circularized probe/target nucleic acid molecules;
  isolating the circularized probe/target nucleic acid molecules;
  linearizing the circularized probe/target nucleic acid molecules, thereby forming linearized probe/target nucleic acid molecules;
  conducting an amplification reaction with the linearized probe/target nucleic acid molecules to generate one or more amplification products, wherein the amplification reaction introduces a barcode sequence to the amplification products; and
  sequencing the amplification products; and
  wherein at least one targeting arm of each of the more than one molecular inversion probe does not hybridize to a same sequence of the nucleic acid.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1
gcacgatccg acggtagtgt                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 2
ccgtaatcgg gaagctgaag                                          20